United States Patent
Ciasulli et al.

(10) Patent No.: US 10,417,076 B2
(45) Date of Patent: *Sep. 17, 2019

(54) ASSET HEALTH SCORE

(71) Applicant: Uptake Technologies, Inc., Chicago, IL (US)

(72) Inventors: John Ciasulli, Chicago, IL (US); Michael Horrell, Chicago, IL (US); Sheng Zhong, Buffalo Grove, IL (US); Jason Kolb, Plainfield, IL (US)

(73) Assignee: Uptake Technologies, Inc., Chicago, IL (US)

(*) Notice: Subject to any disclaimer, the term of this patent is extended or adjusted under 35 U.S.C. 154(b) by 364 days.

This patent is subject to a terminal disclaimer.

(21) Appl. No.: 14/732,258

(22) Filed: Jun. 5, 2015

(65) Prior Publication Data
US 2016/0153806 A1     Jun. 2, 2016

Related U.S. Application Data

(60) Provisional application No. 62/086,155, filed on Dec. 1, 2014, provisional application No. 62/088,651, filed on Dec. 7, 2014.

(51) Int. Cl.
*G06F 11/30* (2006.01)
*G21C 17/00* (2006.01)
(Continued)

(52) U.S. Cl.
CPC ............ *G06F 11/079* (2013.01); *G01D 3/08* (2013.01); *G01M 99/008* (2013.01);
(Continued)

(58) Field of Classification Search
CPC .. G06F 11/079; G06F 11/008; G06F 11/0709; G06F 11/0721; G06F 11/0751;
(Continued)

(56) References Cited

U.S. PATENT DOCUMENTS 5,363,317 A   11/1994 Rice et al.
5,566,092 A   10/1996 Wang et al.
(Continued)

FOREIGN PATENT DOCUMENTS

JP   2000315111   11/2000
JP   2003256367   9/2003
(Continued)

OTHER PUBLICATIONS

"International Search Report for Application No. PCT/US2015/063047, dated Mar. 28, 2016, 3 pages".
(Continued)

*Primary Examiner* — Michael P Nghiem
(74) *Attorney, Agent, or Firm* — Lee Sullivan Shea & Smith LLP

(57) ABSTRACT

Disclosed herein are systems, devices, and methods related to assets and asset operating conditions. In particular, examples involve defining and executing predictive models for outputting health metrics that estimate the operating health of an asset or a part thereof, analyzing health metrics to determine variables that are associated with high health metrics, and modifying the handling of abnormal-condition indicators in accordance with a prediction of a likely response to such abnormal-condition indicators, among other examples.

20 Claims, 16 Drawing Sheets

(51) Int. Cl.

| | | |
|---|---|---|
| *G06F 11/07* | (2006.01) | |
| *G06Q 10/00* | (2012.01) | |
| *G06F 11/26* | (2006.01) | |
| *G06F 11/263* | (2006.01) | |
| *G08B 21/18* | (2006.01) | |
| *G06F 11/00* | (2006.01) | |
| *G01D 3/08* | (2006.01) | |
| *G01M 99/00* | (2011.01) | |
| *G06F 11/20* | (2006.01) | |
| *G06N 5/02* | (2006.01) | |
| *G06N 7/00* | (2006.01) | |
| *H04L 12/707* | (2013.01) | |
| *G06Q 10/06* | (2012.01) | |
| *G06N 5/04* | (2006.01) | |
| *G06Q 10/04* | (2012.01) | |
| *G06Q 50/04* | (2012.01) | |
| *G06Q 50/08* | (2012.01) | |
| *G05B 23/02* | (2006.01) | |

(52) U.S. Cl.
CPC ........ *G05B 23/0254* (2013.01); *G06F 11/008* (2013.01); *G06F 11/0709* (2013.01); *G06F 11/0721* (2013.01); *G06F 11/0751* (2013.01); *G06F 11/0754* (2013.01); *G06F 11/0772* (2013.01); *G06F 11/0787* (2013.01); *G06F 11/0793* (2013.01); *G06F 11/2007* (2013.01); *G06F 11/26* (2013.01); *G06F 11/263* (2013.01); *G06N 5/02* (2013.01); *G06N 5/04* (2013.01); *G06N 7/005* (2013.01); *G06Q 10/04* (2013.01); *G06Q 10/067* (2013.01); *G06Q 10/06312* (2013.01); *G06Q 10/20* (2013.01); *G06Q 50/04* (2013.01); *G06Q 50/08* (2013.01); *G08B 21/18* (2013.01); *H04L 45/22* (2013.01); *G06F 2201/85* (2013.01)

(58) Field of Classification Search
CPC ............. G06F 11/0772; G06F 11/0787; G06F 11/0793; G06F 11/2007; G06F 11/26; G06F 11/263; G01D 3/08; G01M 99/008; G06N 5/02; G06N 5/04; G06N 7/005; G06Q 10/04; G06Q 10/06312; G06Q 10/067; G06Q 10/20; G08B 21/18; H04L 45/22
USPC .......................................................... 702/184
See application file for complete search history.

(56) References Cited

U.S. PATENT DOCUMENTS

| | | | |
|---|---|---|---|
| 5,633,800 | A | 5/1997 | Bankert et al. |
| 5,918,222 | A | 6/1999 | Fukui et al. |
| 6,256,594 | B1 | 7/2001 | Yamamoto et al. |
| 6,336,065 | B1 | 1/2002 | Gibson et al. |
| 6,442,542 | B1 | 8/2002 | Ramani et al. |
| 6,473,659 | B1 | 10/2002 | Shah et al. |
| 6,622,264 | B1 | 9/2003 | Bliley et al. |
| 6,625,500 | B1 | 9/2003 | Li |
| 6,634,000 | B1 | 10/2003 | Jammu et al. |
| 6,643,600 | B2 | 11/2003 | Yanosik et al. |
| 6,650,949 | B1 | 11/2003 | Fera et al. |
| 6,725,398 | B1 | 4/2004 | Varma et al. |
| 6,760,631 | B1 | 7/2004 | Berkowitz et al. |
| 6,775,641 | B2 | 8/2004 | Wegerich et al. |
| 6,799,154 | B1 | 9/2004 | Aragones et al. |
| 6,823,253 | B2 | 11/2004 | Brunell |
| 6,859,739 | B2 | 2/2005 | Wegerich et al. |
| 6,892,163 | B1 | 5/2005 | Herzog et al. |
| 6,947,797 | B2 | 9/2005 | Dean et al. |
| 6,952,662 | B2 | 10/2005 | Wegerich et al. |
| 6,957,172 | B2 | 10/2005 | Wegerich |
| 6,975,962 | B2 | 12/2005 | Wegerich et al. |
| 7,020,595 | B1 | 3/2006 | Adibhatla et al. |
| 7,082,379 | B1 | 7/2006 | Bickford et al. |
| 7,100,084 | B2 | 8/2006 | Unkle et al. |
| 7,107,491 | B2 | 9/2006 | Graichen et al. |
| 7,127,371 | B2 | 10/2006 | Duckert et al. |
| 7,174,233 | B1 | 2/2007 | Blackshear et al. |
| 7,233,886 | B2 | 6/2007 | Wegerich et al. |
| 7,280,941 | B2 | 10/2007 | Bonanni et al. |
| 7,308,385 | B2 | 12/2007 | Wegerich et al. |
| 7,373,283 | B2 | 5/2008 | Herzog et al. |
| 7,403,869 | B2 | 7/2008 | Wegerich et al. |
| 7,409,320 | B2 | 8/2008 | Wegerich |
| 7,415,382 | B1 | 8/2008 | Bickford et al. |
| 7,428,478 | B2 | 9/2008 | Aragones |
| 7,447,666 | B2 | 11/2008 | Wang |
| 7,457,693 | B2 | 11/2008 | Olsen et al. |
| 7,457,732 | B2 | 11/2008 | Aragones et al. |
| 7,509,235 | B2 | 3/2009 | Bonissone et al. |
| 7,536,364 | B2 | 5/2009 | Subbu et al. |
| 7,539,597 | B2 | 5/2009 | Wegerich et al. |
| 7,548,830 | B2 | 6/2009 | Goebel et al. |
| 7,599,762 | B2 * | 10/2009 | Discenzo .............. B66C 13/063 701/1 |
| 7,634,384 | B2 | 12/2009 | Eryurek et al. |
| 7,640,145 | B2 | 12/2009 | Wegerich et al. |
| 7,660,705 | B1 | 2/2010 | Meek et al. |
| 7,725,293 | B2 | 5/2010 | Bonissone et al. |
| 7,729,789 | B2 * | 6/2010 | Blevins ................. G05B 17/02 700/83 |
| 7,739,096 | B2 | 6/2010 | Wegerich et al. |
| 7,756,678 | B2 | 7/2010 | Bonissone et al. |
| 7,822,578 | B2 | 10/2010 | Kasztenny et al. |
| 7,869,908 | B2 | 1/2011 | Walker |
| 7,919,940 | B2 | 4/2011 | Miller et al. |
| 7,941,701 | B2 | 5/2011 | Wegerich et al. |
| 7,962,240 | B2 | 6/2011 | Morrison et al. |
| 8,024,069 | B2 | 9/2011 | Miller et al. |
| 8,050,800 | B2 | 11/2011 | Miller et al. |
| 8,135,481 | B2 * | 3/2012 | Blevins ................. G05B 17/02 700/51 |
| 8,145,578 | B2 | 3/2012 | Pershing et al. |
| 8,229,769 | B1 | 7/2012 | Hopkins |
| 8,234,420 | B2 | 7/2012 | Lueckenbach et al. |
| 8,239,170 | B2 | 8/2012 | Wegerich |
| 8,275,577 | B2 | 9/2012 | Herzog |
| 8,285,402 | B2 | 10/2012 | Lueckenbach et al. |
| 8,311,774 | B2 | 11/2012 | Hines |
| 8,352,216 | B2 | 1/2013 | Subbu et al. |
| 8,532,795 | B2 | 9/2013 | Adavi et al. |
| 8,533,018 | B2 | 9/2013 | Miwa et al. |
| 8,560,494 | B1 | 10/2013 | Downing et al. |
| 8,620,618 | B2 | 12/2013 | Eryurek et al. |
| 8,620,853 | B2 | 12/2013 | Herzog |
| 8,626,385 | B2 | 1/2014 | Humphrey |
| 8,645,276 | B2 | 2/2014 | Wong et al. |
| 8,660,980 | B2 | 2/2014 | Herzog |
| 8,682,454 | B2 | 3/2014 | Fuller et al. |
| 8,689,108 | B1 | 4/2014 | Duffield et al. |
| 8,713,467 | B1 | 4/2014 | Goldenberg et al. |
| 8,786,605 | B1 | 7/2014 | Curtis et al. |
| 8,799,799 | B1 | 8/2014 | Cervelli et al. |
| 8,812,960 | B1 | 8/2014 | Sun et al. |
| 8,825,567 | B2 | 9/2014 | Jiang et al. |
| 8,832,594 | B1 | 9/2014 | Thompson et al. |
| 8,850,000 | B2 | 9/2014 | Collins et al. |
| 8,862,938 | B2 | 10/2014 | Souvannarath |
| 8,868,537 | B1 | 10/2014 | Colgrove et al. |
| 8,886,601 | B1 | 11/2014 | Landau et al. |
| 8,909,656 | B2 | 12/2014 | Kumar et al. |
| 8,917,274 | B2 | 12/2014 | Ma et al. |
| 8,918,246 | B2 | 12/2014 | Friend |
| 8,924,429 | B1 | 12/2014 | Fisher et al. |
| 8,935,201 | B1 | 1/2015 | Fisher et al. |
| 8,937,619 | B2 | 1/2015 | Sharma et al. |
| 8,938,686 | B1 | 1/2015 | Erenrich et al. |
| 9,007,896 | B2 | 4/2015 | North et al. |

(56) References Cited

U.S. PATENT DOCUMENTS

| | | | |
|---|---|---|---|
| 9,260,976 B2* | 2/2016 | Phillips | F02C 7/32 |
| 9,471,452 B2* | 10/2016 | McElhinney | G06F 11/0751 |
| 9,864,665 B2* | 1/2018 | McElhinney | G06F 11/26 |
| 10,176,032 B2* | 1/2019 | Horrell | G06F 11/0751 |
| 2002/0091972 A1 | 7/2002 | Harris et al. | |
| 2002/0152056 A1 | 10/2002 | Herzog et al. | |
| 2003/0055666 A1 | 3/2003 | Roddy et al. | |
| 2003/0126258 A1 | 7/2003 | Conkright et al. | |
| 2004/0181712 A1 | 9/2004 | Taniguchi et al. | |
| 2004/0243636 A1 | 12/2004 | Hasiewicz et al. | |
| 2005/0119905 A1 | 6/2005 | Wong et al. | |
| 2005/0222747 A1 | 10/2005 | Vhora et al. | |
| 2006/0036403 A1 | 2/2006 | Wegerich et al. | |
| 2006/0048018 A1 | 3/2006 | Hosoya et al. | |
| 2006/0293777 A1 | 12/2006 | Breitgand | |
| 2007/0005266 A1* | 1/2007 | Blevins | G05B 17/02 |
| | | | 702/22 |
| 2007/0050115 A1* | 3/2007 | Discenzo | B66C 13/063 |
| | | | 701/50 |
| 2007/0088570 A1* | 4/2007 | Shetty | G05B 23/0254 |
| | | | 705/2 |
| 2007/0263628 A1 | 11/2007 | Axelsson et al. | |
| 2007/0266557 A1 | 11/2007 | Drost et al. | |
| 2007/0288414 A1* | 12/2007 | Barajas | G06N 7/00 |
| | | | 706/46 |
| 2008/0040244 A1 | 2/2008 | Ricciuti et al. | |
| 2008/0059080 A1 | 3/2008 | Greiner et al. | |
| 2008/0059120 A1 | 3/2008 | Xiao et al. | |
| 2008/0097945 A1 | 4/2008 | Greis et al. | |
| 2008/0141066 A1 | 6/2008 | Wood et al. | |
| 2008/0255760 A1* | 10/2008 | Rojicek | G06Q 10/04 |
| | | | 702/3 |
| 2009/0326890 A1* | 12/2009 | Shetty | G05B 17/02 |
| | | | 703/7 |
| 2010/0023239 A1 | 1/2010 | Self et al. | |
| 2010/0114423 A1 | 5/2010 | Boss et al. | |
| 2010/0222899 A1* | 9/2010 | Blevins | G05B 17/02 |
| | | | 700/80 |
| 2011/0080828 A1 | 4/2011 | North et al. | |
| 2011/0276828 A1 | 11/2011 | Tamaki et al. | |
| 2012/0190342 A1 | 7/2012 | Seibert | |
| 2012/0221156 A1 | 8/2012 | Fuller et al. | |
| 2012/0271612 A1 | 10/2012 | Barsoum et al. | |
| 2012/0310597 A1 | 12/2012 | Uchiyama et al. | |
| 2013/0010610 A1 | 1/2013 | Karthikeyan et al. | |
| 2013/0024416 A1 | 1/2013 | Herzog | |
| 2013/0063262 A1 | 3/2013 | Shaikh et al. | |
| 2013/0204808 A1 | 8/2013 | Jiang et al. | |
| 2013/0283773 A1 | 10/2013 | Hague | |
| 2013/0305081 A1 | 11/2013 | Agnihotram et al. | |
| 2013/0325502 A1 | 12/2013 | Robicsek et al. | |
| 2014/0012886 A1 | 1/2014 | Downing et al. | |
| 2014/0032132 A1 | 1/2014 | Stratton et al. | |
| 2014/0060030 A1 | 3/2014 | Ma et al. | |
| 2014/0089035 A1 | 3/2014 | Jericho et al. | |
| 2014/0105481 A1 | 4/2014 | Hasselbusch et al. | |
| 2014/0121868 A1 | 5/2014 | Zhang et al. | |
| 2014/0164851 A1 | 6/2014 | Pelly et al. | |
| 2014/0169398 A1 | 6/2014 | Arndt et al. | |
| 2014/0170617 A1 | 6/2014 | Johnson et al. | |
| 2014/0184643 A1 | 7/2014 | Friend | |
| 2014/0222355 A1 | 8/2014 | Cheim et al. | |
| 2014/0271114 A1* | 9/2014 | Phillips | F02C 7/32 |
| | | | 415/1 |
| 2014/0330600 A1 | 11/2014 | Candas et al. | |
| 2014/0330749 A1 | 11/2014 | Candas et al. | |
| 2014/0351642 A1 | 11/2014 | Bates et al. | |
| 2014/0357295 A1 | 12/2014 | Skomra et al. | |
| 2014/0358601 A1 | 12/2014 | Smiley et al. | |
| 2014/0365191 A1* | 12/2014 | Zyglowicz | G06F 17/5009 |
| | | | 703/7 |
| 2014/0365271 A1* | 12/2014 | Smiley | G06Q 10/0635 |
| | | | 705/7.28 |
| 2015/0046870 A1 | 2/2015 | Goldenberg et al. | |
| 2015/0112903 A1* | 4/2015 | Chan | G06N 5/04 |
| | | | 706/12 |
| 2015/0160098 A1* | 6/2015 | Noda | G05B 23/024 |
| | | | 702/35 |
| 2015/0262060 A1 | 9/2015 | Husain et al. | |
| 2015/0301882 A1 | 10/2015 | Liao et al. | |
| 2016/0078695 A1 | 3/2016 | McClintic et al. | |
| 2016/0154690 A1* | 6/2016 | Horrell | G06F 11/0751 |
| | | | 714/57 |
| 2016/0155098 A1* | 6/2016 | McElhinney | G06F 11/0751 |
| | | | 705/305 |
| 2016/0155315 A1* | 6/2016 | McElhinney | G06F 11/0751 |
| | | | 340/502 |
| 2016/0349330 A1 | 12/2016 | Barfield, Jr. et al. | |
| 2016/0359683 A1 | 12/2016 | Bartfai-Walcott et al. | |
| 2016/0371584 A1* | 12/2016 | Nicholas | G05B 23/02 |
| 2016/0371585 A1* | 12/2016 | McElhinney | G06N 5/02 |
| 2016/0378585 A1* | 12/2016 | McElhinney | G06F 11/0751 |
| | | | 714/37 |
| 2016/0379465 A1* | 12/2016 | McElhinney | G06F 11/0751 |
| | | | 340/502 |

FOREIGN PATENT DOCUMENTS

| | | |
|---|---|---|
| JP | 2008117129 | 5/2008 |
| WO | 2002054223 A1 | 7/2002 |
| WO | WO-02054223 A1 * | 7/2002 |
| WO | 2011117570 | 9/2011 |
| WO | 2013034420 | 3/2013 |
| WO | 2014054051 A1 | 4/2014 |
| WO | WO-2014054051 A1 * | 4/2014 |
| WO | 2014145977 | 9/2014 |
| WO | 2014205497 | 12/2014 |

OTHER PUBLICATIONS

"International Search Report for Application No. PCT/US2015/063052, dated Mar. 17, 2016, 3 pages".

International Searching Authority, Written Opinion dated Mar. 28, 2016, issued in connection with International Application No. PCT/US2015/063047, filed Nov. 30, 2015, 8 pages.

International Searching Authority, Written Opinion dated Mar. 17, 2016, issued in connection with International Application No. PCT/US2015/063052, filed Nov. 30, 2015, 7 pages.

Biswas, "Redundancy-based Approaches in Wireless Multihop Network Design", PhD Dissertation Submitted to Graduate Faculty of North Carolina State University (2014).

Isermann, "Model-based Fault Detection and Diagnosis—Status and Applications", Institute of Automatic Control, Darmstadt University of Technology (2004).

Narasimhan et al, "Combining Model-Based and Feature-Driven Diagnosis Approaches—A Case Study on Electromechanical Actuators", 21st International Workshop on Principles of Diagnosis (2010).

Prentzas et al, Categorizing Approaches Combining Rule-Based and Case-Based Reasoning.

Infor M3 Enterprise Management System, Infor.com (2014).

Infor Equipment, Infor.com (2012).

Infor Introduces Next-Generation Solution for Equipment Dealers and Service Providers, Infor.com (Feb. 20, 2014).

Infor Equipment for Rental, Infor.com (2013).

Waltermire et al, Applying the Continuous Monitoring Technical Reference Model to the Asset, Configuration, and Vulnerability Management Domains (DRAFT), NIST (Jan. 2012).

Duan et al. "Short Paper: Data Mining-based Fault Prediction and Detection on the Grid" High Performance Distributed Computing, 2006 15th IEEE International Symposium on IEEE, 4 pages.

European Patent Office Extended Search Report for EP Application No. 15866135.5 dated Apr. 23, 2018, 9 pages.

Intellectual Property Office of Singapore, Written Opinion dated Jan. 18, 2018, issued in connection with Singapore Application No. 11201708094X, filed on Oct. 2, 2017, 8 pages.

(56) References Cited

OTHER PUBLICATIONS

European Patent Office Examination Report for EP Application No. 158661355 dated Jun. 5, 2019, 8 pages.

* cited by examiner

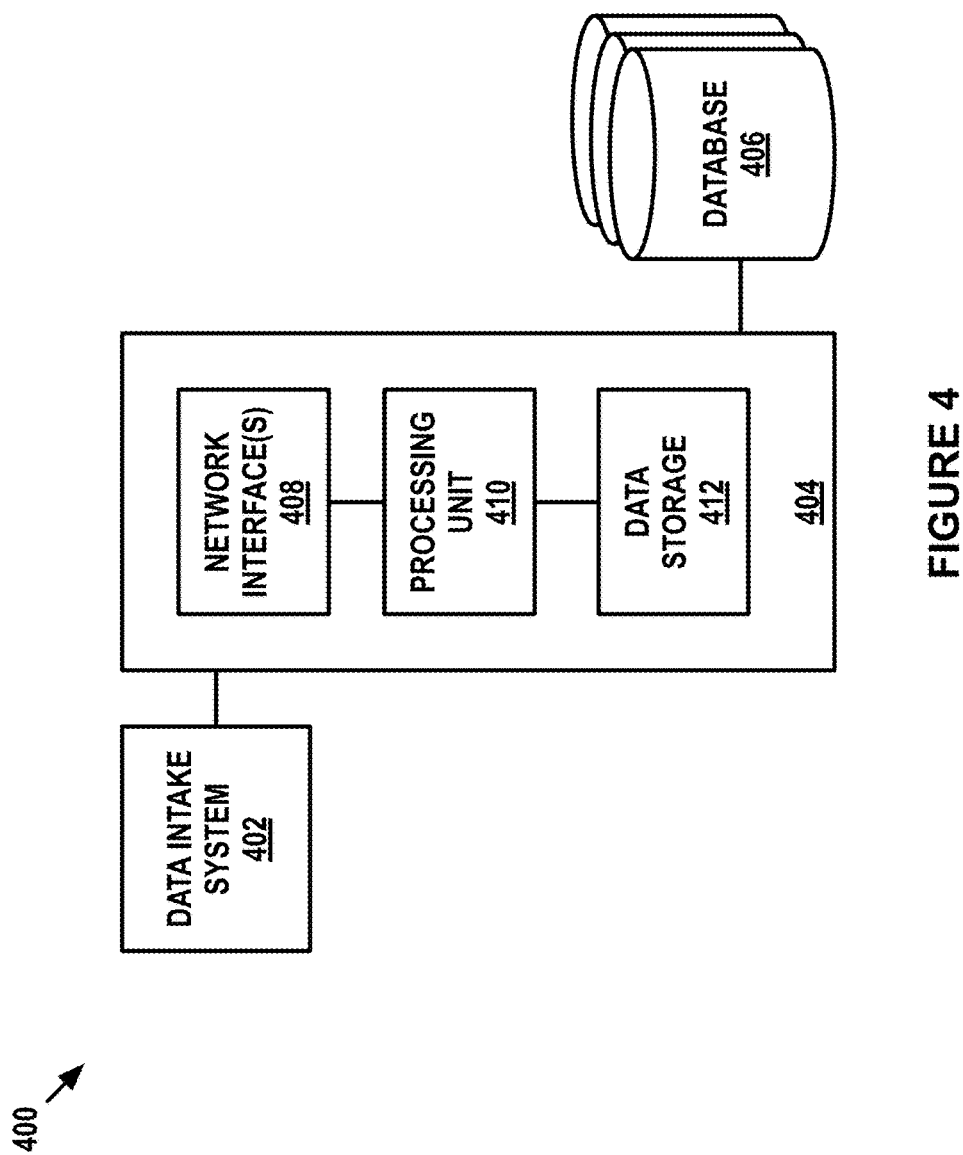

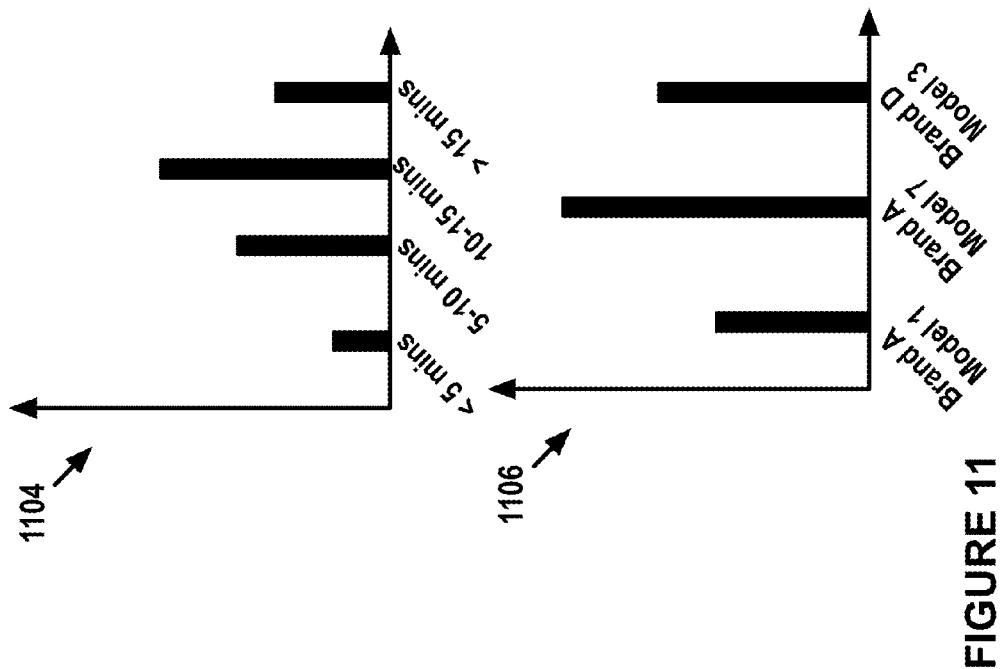
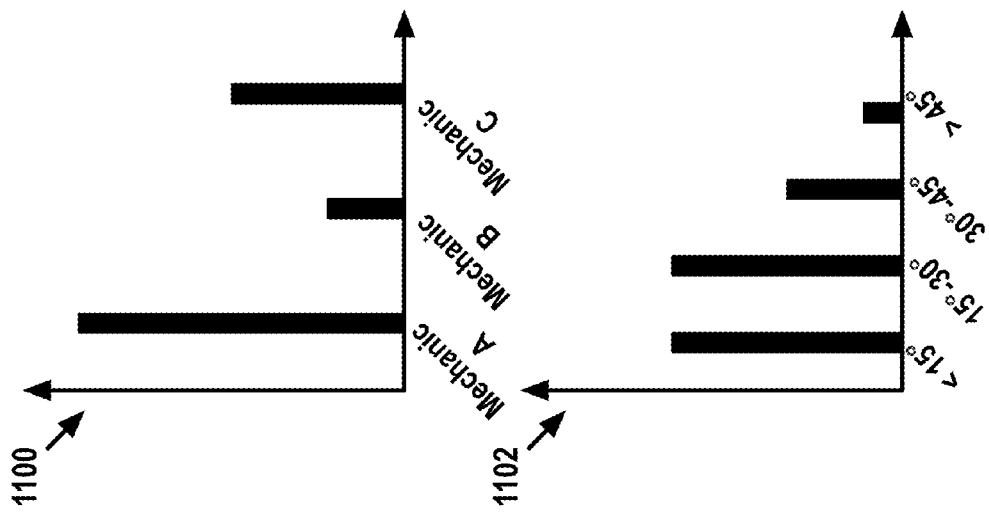
FIGURE 11

ASSET HEALTH SCORE

CROSS REFERENCE TO RELATED APPLICATIONS

This application claims priority to U.S. Provisional Patent Application No. 62/086,155, filed Dec. 1, 2014, entitled Method and Apparatus for Displaying Information Related to Industrial Application Health and Capability Information, and U.S. Provisional Patent Application No. 62/088,651, filed Dec. 7, 2014, entitled Uptake+CAT, each of which is herein incorporated by reference in its entirety.

This application is also related to the following applications filed on the same day as the present application, each of which is incorporated by reference in its entirety: U.S. Non-Provisional patent application Ser. No. 14/732,285, entitled Subsystem Health Score, now U.S. Pat. No. 10,176, 032; pending U.S. Non-Provisional patent application Ser. No. 14/732,303, entitled Historical Health Metrics; and U.S. Non-Provisional patent application Ser. No. 14/732,320, entitled Adaptive Handling of Operating Data, which is now issued as U.S. Pat. No. 9,471,452.

BACKGROUND

Today, machines (also referred to herein as "assets") are ubiquitous in many industries. From locomotives that transfer cargo across countries to medical equipment that helps nurses and doctors to save lives, assets serve an important role in everyday life. Depending on the role that an asset serves, its complexity, and cost, may vary. For instance, some assets may include multiple subsystems that must operate in harmony for the asset to function properly (e.g., an engine, transmission, etc. of a locomotive).

Because of the key role that assets play in everyday life, it is desirable for assets to be repairable with limited downtime. Accordingly, some have developed mechanisms to monitor and detect abnormal conditions within an asset to facilitate repairing the asset, perhaps with minimal downtime.

OVERVIEW

The current approach for monitoring assets generally involves an on-asset computer that receives signals from various sensors distributed throughout the asset that monitor operating conditions of the asset. As one representative example, if the asset is a locomotive, the sensors may monitor parameters such as temperatures, voltages, and speeds, among other examples. If sensor signals from one or more sensors reach certain values, the on-asset computer may then generate an abnormal-condition indicator, such as a "fault code," which is an indication that an abnormal condition has occurred within the asset. In practice, a user typically defines the sensors and respective sensor values associated with each abnormal-condition indicator. That is, the user defines an asset's "normal" operating conditions (e.g., those that do not trigger abnormal-condition indicators) and "abnormal" operating conditions (e.g., those that trigger abnormal-condition indicators).

In general, an abnormal condition may be a defect at an asset or component thereof, which may lead to a failure of the asset and/or component. As such, an abnormal condition may be associated with a given failure, or perhaps multiple failures, in that the abnormal condition is symptomatic of the given failure or failures.

After the on-asset computer generates an abnormal-condition indicator, the indicator and/or sensor signals may be passed to a remote location where a user may receive some indication of the abnormal condition and decide whether to take action. In some cases, the user may also review the sensor signals associated with the abnormal-condition indicator to facilitate diagnosing the cause of the abnormal-condition indicator.

While current asset-monitoring systems are generally effective at triggering abnormal-condition indicators, such systems are typically reactionary. That is, by the time the asset-monitoring system triggers an indicator, a failure within the asset may have already occurred (or is right about to occur), which may lead to costly downtime, among other disadvantages. Moreover, due to the simplistic nature of on-asset abnormality-detection mechanisms in such asset-monitoring systems, current asset-monitoring approaches tend to produce many indicators for "false positives," which may be inefficient when a user is forced to review and respond to these indicators that are not meaningful.

The example systems, devices, and methods disclosed herein seek to help address one or more of these issues. In some examples, a network configuration may include a communication network that facilitates communications between one or more assets, a remote computing system, one or more output systems, and one or more data sources.

As noted above, each asset may include multiple sensors distributed throughout the asset that facilitate monitoring operating conditions of the asset. The asset may then provide data indicative of the asset's operating conditions to the remote computing system, which may be configured to perform one or more operations based on the provided data.

In one aspect, for instance, the remote computing system may be configured to determine a health metric (also referred to herein as a "health score") of a given asset, which may be a single, aggregated parameter that reflects whether a failure will occur at the given asset within a certain period of time into the future. In example implementations, a health metric may indicate a probability that no failures from a group of failures will occur at the given asset. In other example implementations, a health metric may indicate a probability that at least one failure from a group of failures will occur at the given asset.

In general, determining a health metric may involve a "machine-learning" phase, during which the remote computing system may analyze historical operating data for one or more assets to define a model for predicting asset failures, and an asset-monitoring phase, during which the remote computing system uses a given asset's current operating data and the model defined in the machine learning phase to determine the "health score" for the given asset.

In particular, during the machine-learning phase, the remote computing system may be configured to receive operating data from one or more assets over a certain amount of time. The operating data may include sensor data, such as data reflecting the operating temperature of an engine on a locomotive, and may also include abnormal-condition indicators that were generated by the asset's on-asset computer, for instance. Based on this data, the remote computing system may be configured to determine one or more models that indicate operating conditions of the given asset that historically result in a failure at the given asset.

During the asset-monitoring phase, based on the model from the machine-learning phase and operating data from the given asset, the remote computing system may be configured to determine a probability that one or more particular failures may occur at the given asset within a preselected period of time into the future (e.g., within the next 2 weeks). In some cases, the particular failures may be "high impact" events, which are events that could cause an asset to be inoperable when they occur. From the determined failure probability, the remote computing system may determine a single, aggregated health metric for the given asset that indicates whether a failure will occur within the preselected period of time.

The remote computing system may be configured to dynamically update this health metric based on the most recent operating conditions of the given asset. That is, as the actual operating conditions of the asset change, the probability that one or more of the particular failures might occur (and thus the health metric) may change accordingly.

In particular, the remote computing system may receive operating data from the asset, perhaps in real-time. Based on the operating data and the determined model, the remote computing system may be configured to re-calculate the probability that one or more of the particular failures may occur. In the event that the probability has changed, the remote computing system may update the health metric accordingly. This process of dynamically updating the health metric may occur continuously over the course of the asset's operable life.

The remote computing system may further be configured to use the health metric to trigger a number of actions. In some cases, for instance, the remote computing system may facilitate causing an output system to output an indication of a health metric for a given asset, perhaps in conjunction with abnormal-condition indicators and/or sensor data for the given asset.

In another case, the remote computing system may be configured to generate an alert based on the health metric. For example, the remote computing system may be configured to send an alert message to an output device in the event that the health metric is approaching or has reached a health threshold, which may in turn cause the output device to output a visual and/or audible alert to the user. Other examples are also possible.

In yet another case, the remote computing system may be configured to use the health metric to trigger various types of preventative actions. For example, in the event that the health metric has reached a health threshold, the remote computing system may be configured to facilitate causing an output device to display one or more recommended actions that may affect the health metric, facilitate generating a work order to repair the asset, facilitate ordering a part for the asset, and/or transmit to the asset one or more commands that cause the asset to modify its operation. Other preventative actions are also possible.

In addition or in alternative to determining a single, aggregated "health score" for a given asset, the remote computing system may also be configured to determine individual "health scores" for respective subsystems of the given asset based on operating data from the asset, where each individual health score indicates a single, aggregated parameter that reflects whether a failure will occur at the particular subsystem of the given asset within a certain period of time into the future.

The remote computing system may be configured to determine an individual heath score for a given subsystem in various manners. For example, the remote computing system may determine a failure model for the given subsystem based on operating data that is particular to the given subsystem and then determine a subsystem health metric in a manner similar to that discussed above for the asset-level health metric. However, the remote computing system may be configured to determine an individual heath score for the given subsystem in other manners as well.

In some cases, the remote computing system may also be configured to use the individual subsystem-level health metrics for a given asset to determine an asset-level health metric. The remote computing system may be configured to weight the individual subsystem-level health metrics in various manners. For example, the remote computing system may be configured to weight certain subsystem health metrics different than others based on the relative importance of the corresponding subsystem to the overall operation of the asset. This in turn may result in a more accurate asset-level health metric.

As with the asset-level health metric, the remote computing system may be configured to dynamically update the subsystem-level health metrics and use the subsystem-level health metrics to trigger actions similar to those discussed above. However, the subsystem-level health metrics may also allow the remote computing system to trigger more granular and/or additional actions relative to the asset-level actions. Moreover, the subsystem-level health metrics may allow for a more efficacious preventative action by detecting an abnormality at a subsystem-level, which typically might not be detected at an asset-level until sometime later.

In another aspect, the remote computing system may be configured to store historical asset- and/or subsystem-level health metric data for one or more assets. This historical data may then be used for various purposes.

In one example, the remote computing system may be configured to facilitate causing an output system to provide various visualizations based on the stored historical data. For instance, the remote computing system may be configured to facilitate causing an output system to display a graphical representation of historical asset- and/or subsystem-level health metrics for a given asset (or a group of assets) over a given time window.

In another example, the remote computing system may be configured to perform analytics on this stored historical data to identify correlations between health metrics and certain asset-related variables, such as asset class (e.g., brand, model, etc.), a mechanic that works on the asset, and environmental conditions in which the asset is operated, among other examples. For example, based on this stored historical data, the remote computing system may determine that certain classes of assets correlate to relatively high health metrics and/or that certain other classes of assets correlate to relatively low health metrics. As another example, based on this stored historical data, the remote computing system may determine that certain mechanics are responsible for larger improvements in asset health metrics and/or that certain other mechanics are responsible for smaller improvements in asset health metrics. Many other examples are possible as well.

In example implementations, the remote computing system may be configured to perform various operations based on the historical health metric analytics, such as recommending particular classes of assets for particular tasks, optimizing asset repair schedules, and recommending particular repair shops and/or mechanics to service particular problems, among other operations.

In yet another aspect, the remote computing system may be configured to receive feedback data from one or more output systems and then intelligently perform one or more operations based on this feedback data. For example, as noted above, the remote computing system may be configured to recommend and/or trigger various types of preventative actions for a given asset. In this example, the remote computing system may be configured to receive feedback data indicating whether a preventative action successfully prevented an asset failure and then update the health metric model and/or the actions triggered by the health metric based on this feedback data.

In another example, as noted above, the remote computing system may be configured to facilitate causing an output system to display abnormal-condition indicators (e.g., fault codes) for a given asset, perhaps along with recommended actions corresponding to such indicators. As noted above, however, traditional asset-monitoring systems may generate indicators for "false positives" (e.g., abnormal conditions that do not require remedial action and thus are not of interest to a user), which may distract the user from meaningful indicators and/or may desensitize the user's response to indicators. Thus, the remote computing system may be configured to receive feedback data regarding how users respond to particular indicators and then intelligently adjust the manner in which certain indicators are displayed to help improve a user's operation of an asset.

For instance, when presenting a user with an abnormal-condition indicator, an output system may present the user with options that allow the user to dismiss the alert (e.g., by selecting a "Disregard" icon or the like), to take action on the alert (e.g., by selecting a "Resolve" icon or the like), or to ignore the alert (e.g., by making no selection for a predetermined amount of time). The output system may be configured to provide the remote computing system with feedback data indicative of the user's decisions regarding displayed indicator. In turn, the remote computing system may aggregate and perform analytics on such data, perhaps for one or more users reviewing indicators, to identify correlations between indicators and user responses (e.g., response patterns).

Thereafter, the remote computing system may adjust the manner in which certain abnormal-condition indicators are displayed based on the response patterns. For instance, if the response patterns indicate that users typically disregard or ignore a particular type of indicator, the remote computing system may instruct an output device to handle any indicators of that type in accordance with this response pattern, e.g., by displaying the indicator with a recommendation to disregard or simply just suppressing the indicator (either immediately or after a predetermined number of "Disregard" responses by a user).

Before instructing an output device to adjust the manner in which an abnormal-condition indicator is displayed, the remote computing system may also take other information into account, such as the nature of the indicator, the subsystem(s) associated with the indicator, or the like. For instance, the remote computing system may dictate that some types of indicators require a larger number of "Disregard" responses before being suppressed, whereas other types of indicators require a smaller number of "Disregard" responses before being suppressed. Other examples are also possible.

As discussed above, examples provided herein are related to asset monitoring. In one aspect, a computing system is provided. The computing system comprises at least one processor, a non-transitory computer-readable medium, and program instructions stored on the non-transitory computer-readable medium. The program instructions are executable by the at least one processor to cause the computing system to: (a) receive sensor data indicating at least one operating condition of an asset at a reference time, (b) based on the received sensor data and historical operating data, determine a health metric indicating whether a failure from a group of failures will occur at the asset within a period of time after the reference time, wherein the historical operating data comprises (i) historical abnormal-condition data associated with a failure that occurred at the asset at a past time and (ii) historical sensor data indicating at least one operating condition of the asset at the past time, and (c) transmit to a computing device health-metric data indicating the determined health metric to facilitate causing the computing device to display a representation of the determined health metric.

In another aspect, a non-transitory computer-readable medium is provided having instructions stored thereon that are executable to cause a computing system to: (a) receive sensor data indicating at least one operating condition of an asset at a reference time, (b) based on the received sensor data and historical operating data, determine a health metric indicating whether a failure from a group of failures will occur at the asset within a period of time after the reference time, wherein the historical operating data comprises (i) historical abnormal-condition data associated with a failure that occurred at the asset at a past time and (ii) historical sensor data indicating at least one operating condition of the asset at the past time, and (c) transmit to a computing device health-metric data indicating the determined health metric to facilitate causing the computing device to display a representation of the determined health metric.

In yet another aspect, a computer-implemented method is provided. The method comprises (a) receiving sensor data indicating at least one operating condition of an asset at a reference time, (b) based on the received sensor data and historical operating data, determining a health metric indicating whether a failure from a group of failures will occur at the asset within a period of time after the reference time, wherein the historical operating data comprises (i) historical abnormal-condition data associated with a failure that occurred at the asset at a past time and (ii) historical sensor data indicating at least one operating condition of the asset at the past time, and (c) transmitting to a computing device health-metric data indicating the determined health metric to facilitate causing the computing device to display a representation of the determined health metric.

One of ordinary skill in the art will appreciate these as well as numerous other aspects in reading the following disclosure.

BRIEF DESCRIPTION OF THE DRAWINGS

FIG. 4 depicts a simplified block diagram of an example analytics system.

FIG. 11 depicts conceptual illustrations of data that results from incrementing variable counters.

DETAILED DESCRIPTION

The following disclosure makes reference to the accompanying figures and several exemplary scenarios. One of ordinary skill in the art will understand that such references are for the purpose of explanation only and are therefore not meant to be limiting. Part or all of the disclosed systems, devices, and methods may be rearranged, combined, added to, and/or removed in a variety of manners, each of which is contemplated herein.

I. Example Network Configuration

Figure 1:
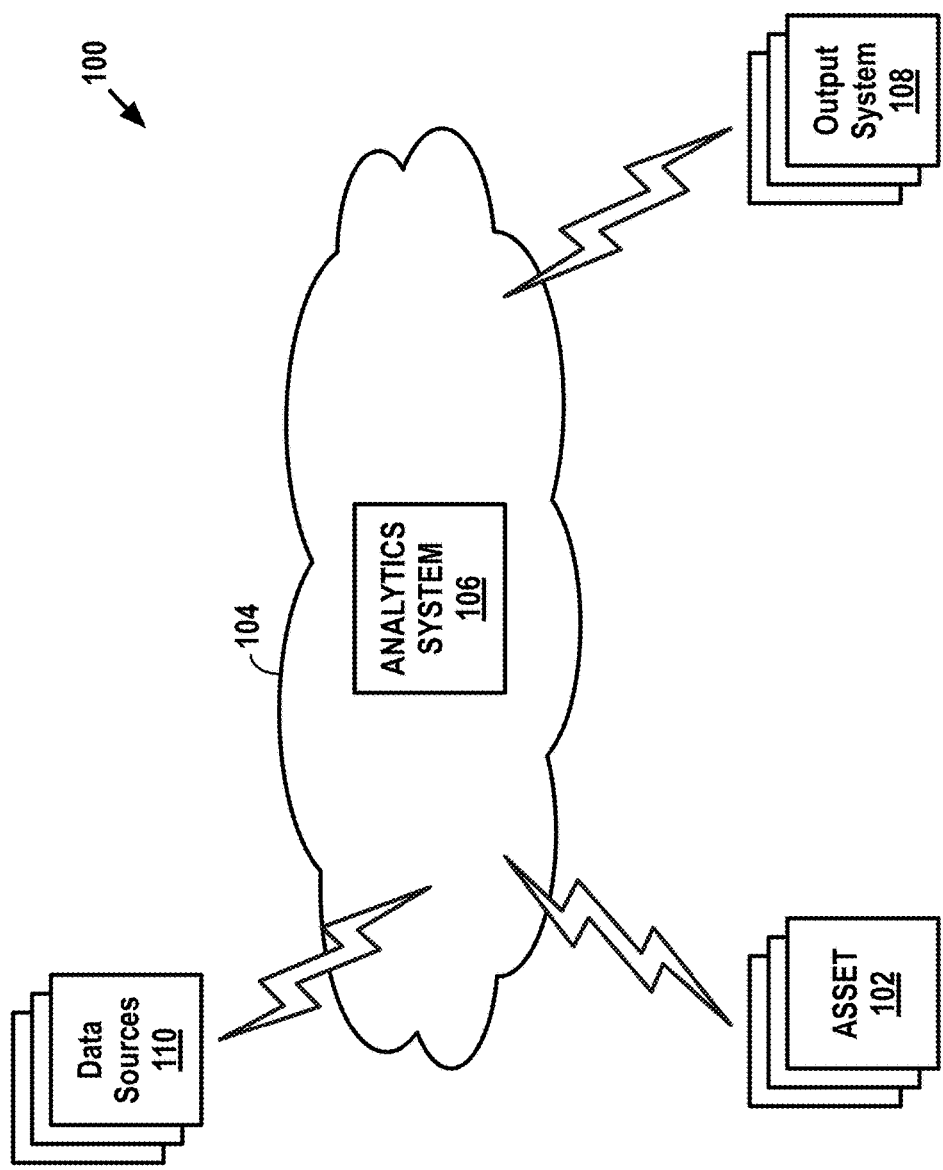
FIG. 1 depicts an example network configuration in which example embodiments may be implemented.

Turning now to the figures, FIG. 1 depicts an example network configuration 100 in which example embodiments may be implemented. As shown, the network configuration 100 includes one or more assets 102, a communication network 104, a remote computing system 106 that may take the form of an analytics system, one or more output systems 108, and one or more data sources 110.

The communication network 104 may communicatively connect each of the components in the network configuration 100. For instance, the assets 102 may communicate with the analytics system 106 via the communication network 104. In some cases, the assets 102 may communicate with one or more intermediary systems, such as a client server (not pictured), that in turn communicates with the analytics system 106. Likewise, the analytics system 106 may communicate with the output systems 108 via the communication network 104. In some cases, the analytics system 106 may communicate with one or more intermediary systems, such as a host server (not pictured), that in turn communicates with the output systems 108. Many other configurations are also possible.

In general, an asset 102 may take the form of any device configured to perform one or more operations (which may be defined based on the field) and may also include equipment configured to transmit data indicative of one or more operating conditions of the asset 102. In some examples, an asset 102 may include one or more subsystems configured to perform one or more respective operations. In practice, multiple subsystems may operate in parallel or sequentially in order for an asset 102 to operate.

Example assets may include transportation machines (e.g., locomotives, aircrafts, semi-trailer trucks, ships, etc.), industrial machines (e.g., mining equipment, construction equipment, etc.), medical machines (e.g., medical imaging equipment, surgical equipment, medical monitoring systems, medical laboratory equipment, etc.), and utility machines (e.g., turbines, solar farms, etc.), among other examples. Those of ordinary skill in the art will appreciate that these are but a few examples of assets and that numerous others are possible and contemplated herein.

In example implementations, the assets 102 shown in FIG. 1 may all be of the same type (e.g., a fleet of locomotives or aircrafts, a group of wind turbines, or a set of MRI machines, among other examples) and perhaps may be of the same class (e.g., same brand and/or model). In other examples, the assets 102 shown in FIG. 1 may differ by type, by brand, by model, etc. The assets 102 are discussed in further detail below with reference to FIG. 2.

As shown, the assets 102, and perhaps other data sources 110, may communicate with the analytics system 106 via the communication network 104. In general, the communication network 104 may include one or more computing systems and network infrastructure configured to facilitate transferring data between network components. The communication network 104 may be or may include one or more Wide-Area Networks (WANs) and/or Local-Area Networks (LANs), which may be wired and/or wireless. In some examples, the communication network 104 may include one or more cellular networks and/or the Internet, among other networks. The communication network 104 may operate according to one or more communication protocols, such as LTE, CDMA, WiMax, WiFi, Bluetooth, HTTP, TCP, and the like. Although the communication network 104 is shown as a single network, it should be understood that the communication network 104 may include multiple, distinct networks that are themselves communicatively linked. The communication network 104 could take other forms as well.

As noted above, the analytics system 106 may be configured to receive data from the assets 102 and the data sources 110. Broadly speaking, the analytics system 106 may include one or more computing systems, such as servers and databases, configured to receive, process, analyze, and output data. The analytics system 106 may be configured according to a given dataflow technology, such as .NET or Nifi, among other examples. The analytics system 106 is discussed in further detail below with reference to FIG. 3.

As shown, the analytics system 106 may be configured to transmit data to the assets 102 and/or to the output systems 108. The particular data transmitted to the assets 102 and/or to the output systems 108 may take various forms and will be described in further detail below.

In general, an output system 108 may take the form of a computing system or device configured to receive data and provide some form of output. The output system 108 may take various forms. In one example, one or more of the output systems 108 may be or include an output device configured to receive data and provide an audible, visual, and/or tactile output in response to the data. In general, an output device may include one or more input interfaces configured to receive user input, and the output device may be configured to transmit data through the communication network 104 based on such user input. Examples of output devices include tablets, smartphones, laptop computers, other mobile computing devices, desktop computers, smart TVs, and the like.

Another example of an output system 108 may take the form of a work-order system configured to output a request for a mechanic or the like to repair an asset. Yet another example of an output system 108 may take the form of a parts-ordering system configured to place an order for a part of an asset and output a receipt thereof. Numerous other output systems are also possible.

The one or more data sources 110 may be configured to communicate with the analytics system 106. In general, a data source 110 may be or include one or more computing systems configured to collect, store, and/or provide to other systems, such as the analytics system 106, data that may be relevant to the functions performed by the analytics system 106. The data source 110 may be configured to generate and/or obtain data independently from the assets 102. As such, the data provided by the data sources 110 may be referred to herein as "external data." The data source 110 may be configured to provide current and/or historical data. In practice, the analytics system 106 may receive data from a data source 110 by "subscribing" to a service provided by the data source. However, the analytics system 106 may receive data from a data source 110 in other manners as well.

Examples of data sources 110 include environment data sources, asset-management data sources, and other data sources. In general, environment data sources provide data indicating some characteristic of the environment in which assets are operated. Examples of environment data sources include weather-data servers, global navigation satellite systems (GNSS) servers, map-data servers, and topography-data servers that provide information regarding natural and artificial features of a given area, among other examples.

In general, asset-management data sources provide data indicating events or statuses of entities that may affect the operation or maintenance of assets (e.g., when and where an asset may operate or receive maintenance). Examples of asset-management data sources include traffic-data servers that provide information regarding air, water, and/or ground traffic, asset-schedule servers that provide information regarding expected routes and/or locations of assets on particular dates and/or at particular times, defect detector systems (also known as "hotbox" detectors) that provide information regarding one or more operating conditions of an asset that passes in proximity to the defect detector system, part-supplier servers that provide information regarding parts that particular suppliers have in stock and prices thereof, and repair-shop servers that provide information regarding repair shop capacity and the like, among other examples.

Examples of other data sources include power-grid servers that provide information regarding electricity consumption and external databases that store historical operating data for assets, among other examples. One of ordinary skill in the art will appreciate that these are but a few examples of data sources and that numerous others are possible.

It should be understood that the network configuration 100 is one example of a network in which embodiments described herein may be implemented. Numerous other arrangements are possible and contemplated herein. For instance, other network configurations may include additional components not pictured and/or more or less of the pictured components.

II. Example Asset

Figure 2:
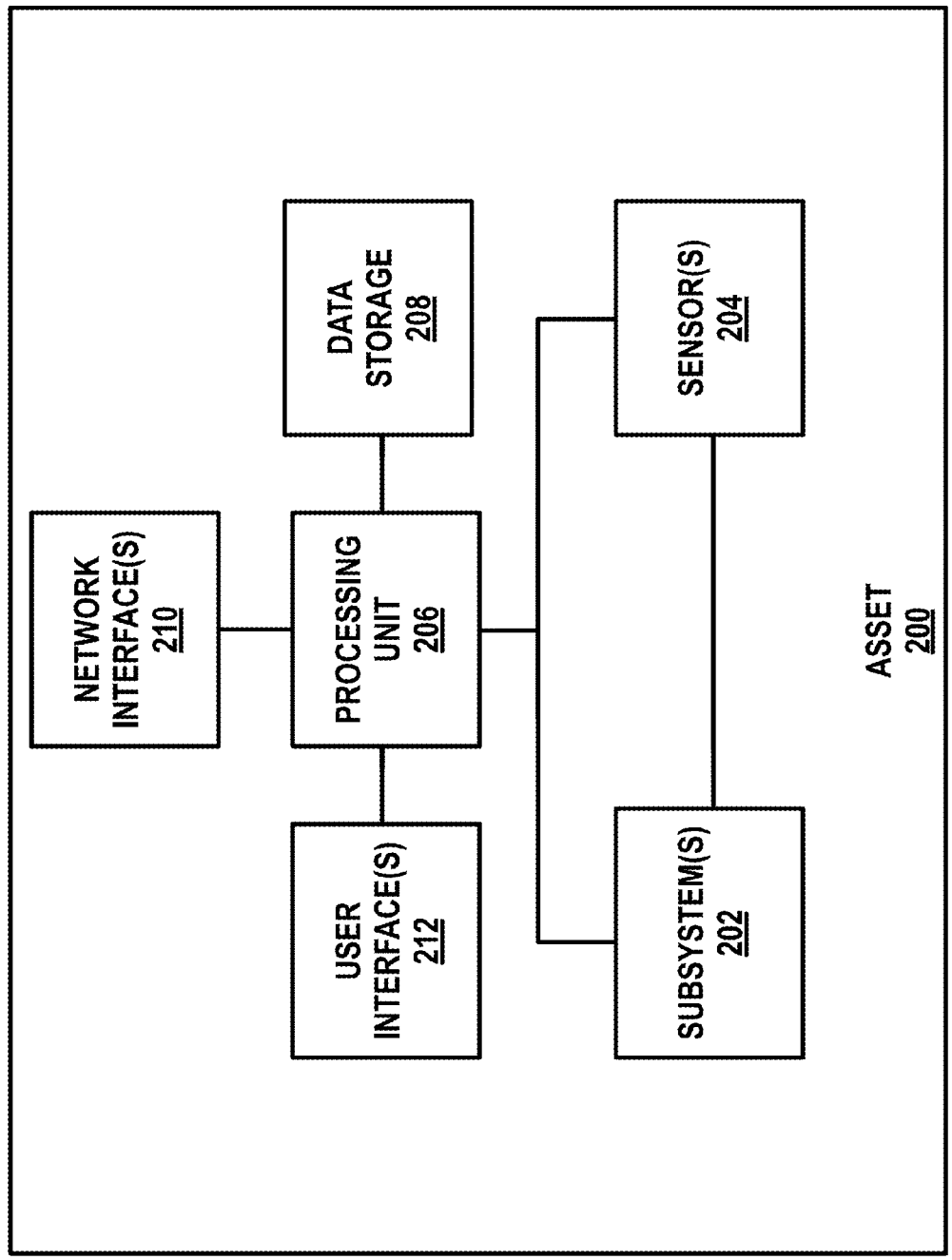
FIG. 2 depicts a simplified block diagram of an example asset.

Turning to FIG. 2, a simplified block diagram of an example asset 200 is depicted. The asset 200 may be one of the assets 102 from FIG. 1. As shown, the asset 200 may include one or more subsystems 202, one or more sensors 204, a processing unit 206, data storage 208, one or more network interfaces 210, and one or more user interfaces 212, all of which may be communicatively linked by a system bus, network, or other connection mechanism. One of ordinary skill in the art will appreciate that the asset 200 may include additional components not shown and/or more or less of the depicted components.

Broadly speaking, the asset 200 may include one or more electrical, mechanical, and/or electromechanical components configured to perform one or more operations. In some cases, one or more components may be grouped into a given subsystem 202.

Generally, a subsystem 202 may include a group of related components that are part of the asset 200. A single subsystem 202 may independently perform one or more operations or the single subsystem 202 may operate along with one or more other subsystems to perform one or more operations. Typically, different types of assets, and even different classes of the same type of assets, may include different subsystems. For instance, in the context of transportation assets, examples of subsystems 202 may include engines, transmissions, drivetrains, fuel systems, battery systems, exhaust systems, braking systems, electrical systems, signal processing systems, generators, gear boxes, rotors, and hydraulic systems, among numerous other examples.

As suggested above, the asset 200 may be outfitted with various sensors 204 that are configured to monitor operating conditions of the asset 200. In some cases, some of the sensors 204 may be grouped based on a particular subsystem 202. In this way, the group of sensors 204 may be configured to monitor operating conditions of the particular subsystem 202.

In general, a sensor 204 may be configured to detect a physical property, which may be indicative of one or more operating conditions of the asset 200, and provide an indication, such as an electrical signal, of the detected physical property. In operation, the sensors 204 may be configured to obtain measurements continuously, periodically (e.g., based on a sampling frequency), and/or in response to some triggering event. In some examples, the sensors 204 may be preconfigured with operating parameters for performing measurements and/or may perform measurements in accordance with operating parameters provided by the processing unit 206 (e.g., sampling signals that instruct the sensors 204 to obtain measurements). In examples, different sensors 204 may have different operating parameters (e.g., some sensors may sample based on a first frequency, while other sensors sample based on a second, different frequency). In any event, the sensors 204 may be configured to transmit electrical signals indicative of a measured physical property to the processing unit 206. The sensors 204 may continuously or periodically provide such signals to the processing unit 206.

For instance, sensors 204 may be configured to measure physical properties such as the location and/or movement of the asset 200, in which case the sensors may take the form of GNSS sensors, dead-reckoning-based sensors, accelerometers, gyroscopes, pedometers, magnetometers, or the like.

Additionally, various sensors 204 may be configured to measure other operating conditions of the asset 200, examples of which may include temperatures, pressures, speeds, friction, power usages, fuel usages, fluid levels, runtimes, voltages and currents, magnetic fields, electric fields, and power generation, among other examples. One of ordinary skill in the art will appreciate that these are but a few example operating conditions that sensors may be configured to measure. Additional or fewer sensors may be used depending on the industrial application or specific asset.

The processing unit 206 may include one or more processors, which may take the form of a general- or special-purpose processor. Examples of processors may include microprocessors, application-specific integrated circuits, digital signal processors, and the like. In turn, the data storage 208 may be or include one or more non-transitory computer-readable storage media, such as optical, magnetic, organic, or flash memory, among other examples.

The processing unit 206 may be configured to store, access, and execute computer-readable program instructions stored in the data storage 208 to perform the operations of an asset described herein. For instance, as suggested above, the processing unit 206 may be configured to receive respective sensor signals from the sensors 204. The processing unit 206 may be configured to store sensor data in and later access it from the data storage 208.

The processing unit 206 may also be configured to determine whether received sensor signals trigger any abnormal-condition indicators, such as fault codes. For instance, the processing unit 206 may be configured to store in the data storage 208 abnormal-condition rules (e.g., fault-code rules), each of which include a given abnormal-condition indicator representing a particular abnormal condition and respective sensor criteria that trigger the abnormal-condition indicator. That is, each abnormal-condition indicator corresponds with one or more sensor measurement values that must be satisfied before the abnormal-condition indicator is triggered. In practice, the asset 200 may be pre-programmed with the abnormal-condition rules and/or may receive new abnormal-condition rules or updates to existing rules from a computing system, such as the analytics system 106.

In any event, the processing unit 206 may be configured to determine whether received sensor signals trigger any abnormal-condition indicators. That is, the processing unit 206 may determine whether received sensor signals satisfy any sensor criteria. When such a determination is affirmative, the processing unit 206 may generate abnormal-condition data and may also cause the asset's user interface 212 to output an indication of the abnormal condition, such as a visual and/or audible alert. Additionally, the processing unit 206 may log the occurrence of the abnormal-condition indicator in the data storage 208, perhaps with a timestamp.

Figure 3:
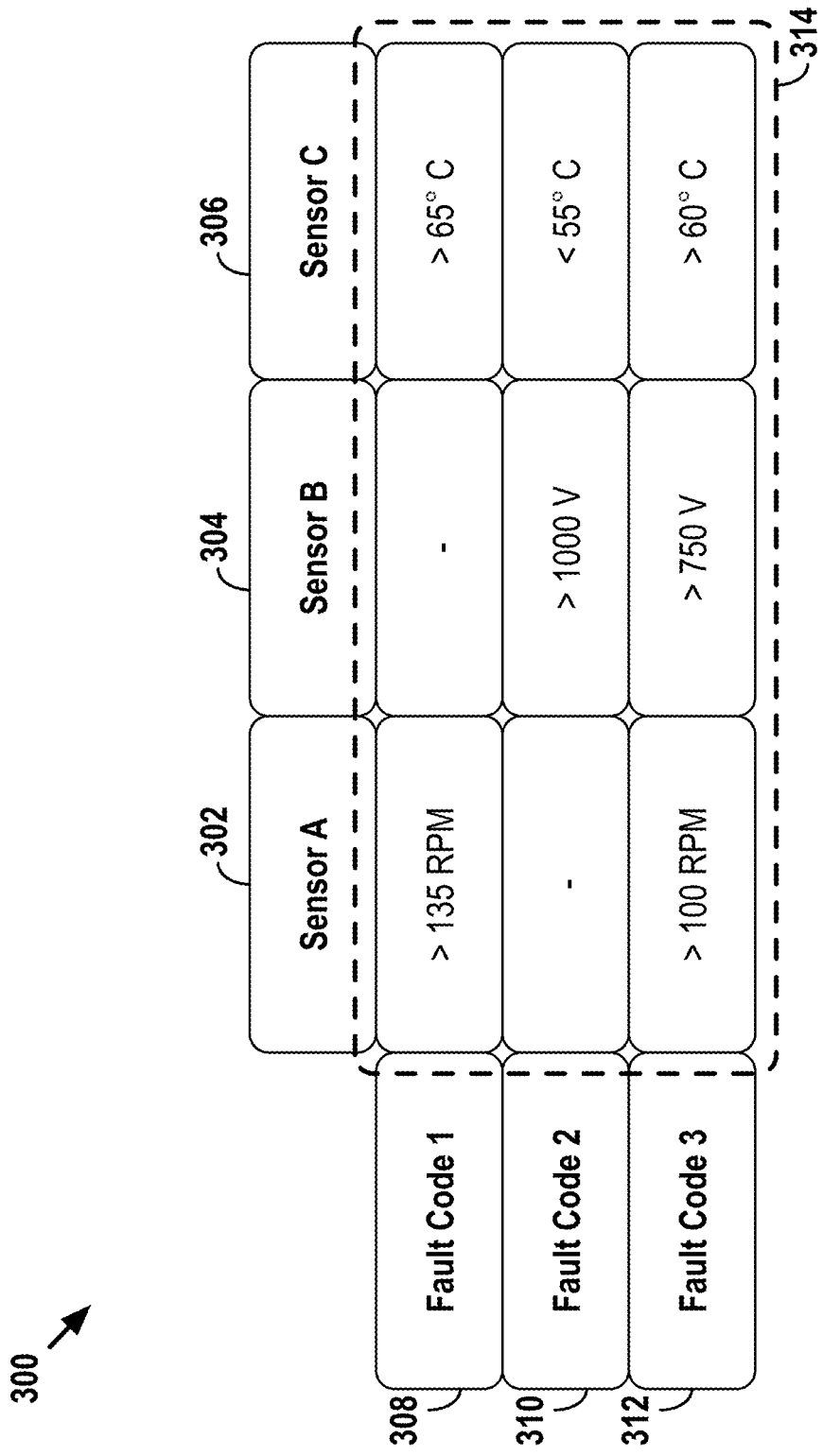
FIG. 3 depicts a conceptual illustration of example abnormal-condition indicators and sensor criteria.

FIG. 3 depicts a conceptual illustration of example abnormal-condition indicators and respective sensor criteria for an asset. In particular, FIG. 3 depicts a conceptual illustration of example fault codes. As shown, table 300 includes columns 302, 304, and 306 that correspond to Sensors A, B, and C, respectively, and rows 308, 310, and 312 that correspond to Fault Codes 1, 2, and 3, respectively. Entries 314 then specify sensor criteria (e.g., sensor value thresholds) that correspond to the given fault codes.

For example, Fault Code 1 will be triggered when Sensor A detects a rotational measurement greater than 135 revolutions per minute (RPM) and Sensor C detects a temperature measurement greater than 65° Celsius (C), Fault Code 2 will be triggered when Sensor B detects a voltage measurement greater than 1000 Volts (V) and a temperature measurement less than 55° C., and Fault Code 3 will be triggered when Sensor A detects a rotational measurement greater than 100 RPM, a voltage measurement greater than 750 V, and a temperature measurement greater than 60° C. One of ordinary skill in the art will appreciate that FIG. 3 is provided for purposes of example and explanation only and that numerous other fault codes and/or sensor criteria are possible and contemplated herein.

Referring back to FIG. 2, the processing unit 206 may be configured to carry out various additional functions for managing and/or controlling operations of the asset 200 as well. For example, the processing unit 206 may be configured to provide instruction signals to the subsystems 202 and/or the sensors 204 that cause the subsystems 202 and/or the sensors 204 to perform some operation, such as modifying a throttle position or a sensor-sampling rate. Moreover, the processing unit 206 may be configured to receive signals from the subsystems 202, the sensors 204, the network interfaces 210, and/or the user interfaces 212 and based on such signals, cause an operation to occur. Other functionalities of the processing unit 206 are discussed below.

The one or more network interfaces 210 may be configured to provide for communication between the asset 200 and various network components connected to communication network 104. For example, at least one network interface 210 may be configured to facilitate wireless communications to and from the communication network 104 and may thus take the form of an antenna structure and associated equipment for transmitting and receiving various over-the-air signals. Other examples are possible as well. In practice, the one or more network interfaces 210 may be configured according to a communication protocol, such as any of those described above.

The one or more user interfaces 212 may be configured to facilitate user interaction with the asset 200 and may also be configured to facilitate causing the asset 200 to perform an operation in response to user interaction. Examples of user interfaces 212 include touch-sensitive interfaces, mechanical interfaces (e.g., levers, buttons, wheels, dials, keyboards, etc.), and other input interfaces (e.g., microphones), among other examples. In some cases, the one or more user interfaces 212 may include or provide connectivity to output components, such as display screens, speakers, headphone jacks, and the like.

One of ordinary skill in the art will appreciate that the asset 200 shown in FIG. 2 is but one example of a simplified representation of an asset and that numerous others are also possible. For instance, in some examples, an asset may include a data acquisition system configured to obtain sensor signals from the sensors where the data acquisition system operates independently from a central controller (such as the processing unit 206) that controls the operations of the asset.

III. Example Analytics System

Referring now to FIG. 4, a simplified block diagram of an example analytics system 400 is depicted. As suggested above, the analytics system 400 may include one or more computing systems communicatively linked and arranged to carry out various operations described herein. Specifically, as shown, the analytics system 400 may include a data intake system 402, a data science system 404, and one or more databases 406. These system components may be communicatively coupled via one or more wireless and/or wired connections.

The data intake system 402 may generally function to receive and process data and output data to the data science system 404. As such, the data intake system 402 may include one or more network interfaces configured to receive data from various network components of the network configuration 100, such as a number of different assets 102 and/or data sources 110. Specifically, the data intake system 402 may be configured to receive analog signals, data streams, and/or network packets, among other examples. As such, the network interfaces may include one or more wired network interfaces, such as a port or the like, and/or wireless network interfaces, similar to those described above. In some examples, the data intake system 402 may be or include components configured according to a given dataflow technology, such as a Nifi receiver or the like.

The data intake system 402 may include one or more processing components configured to perform one or more operations. Example operations may include compression and/or decompression, encryption and/or de-encryption, analog-to-digital and/or digital-to-analog conversion, filtration, and amplification, among other operations. Moreover, the data intake system 402 may be configured to parse, sort, organize, and/or route data based on data type and/or characteristics of the data. In some examples, the data intake system 402 may be configured to format, package, and/or route data based on one or more characteristics or operating parameters of the data science system 404.

In general, the data received by the data intake system 402 may take various forms. For example, the payload of the data may include a single sensor measurement, multiple sensor measurements and/or one or more fault codes. Other examples are also possible.

Moreover, the received data may include certain characteristics, such as a source identifier and a timestamp (e.g., a date and/or time at which the information was obtained). For instance, a unique identifier (e.g., a computer generated alphabetic, numeric, alphanumeric, or the like identifier) may be assigned to each asset, and perhaps to each sensor. Such identifiers may be operable to identify the asset, or sensor, from which data originates. In some cases, another characteristic may include the location (e.g., GPS coordinates) at which the information was obtained. Data characteristics may come in the form of signal signatures or metadata, among other examples.

The data science system 404 may generally function to receive (e.g., from the data intake system 402) and analyze data and based on such analysis, cause one or more operations to occur. As such, the data science system 404 may include one or more network interfaces 408, a processing unit 410, and data storage 412, all of which may be communicatively linked by a system bus, network, or other connection mechanism. In some cases, the data science system 404 may be configured to store and/or access one or more application program interfaces (APIs) that facilitate carrying out some of the functionality disclosed herein.

The network interfaces 408 may be the same or similar to any network interface described above. In practice, the network interfaces 408 may facilitate communication between the data science system 404 and various other entities, such as the data intake system 402, the databases 406, the assets 102, the output systems 108, etc.

The processing unit 410 may include one or more processors, such as any of the processors described above. In turn, the data storage 412 may be or include one or more non-transitory computer-readable storage media, such as any of the examples provided above. The processing unit 410 may be configured to store, access, and execute computer-readable program instructions stored in the data storage 412 to perform the operations of an analytics system described herein.

In general, the processing unit 410 may be configured to perform analytics on data received from the data intake system 402. To that end, the processing unit 410 may be configured to execute one or more modules, which may each take the form of one or more sets of program instructions that are stored in the data storage 412. The modules may be configured to facilitate causing an outcome to occur based on the execution of the respective program instructions. An example outcome from a given module may include outputting data into another module, updating the program instructions of the given module and/or of another module, and outputting data to a network interface 408 for transmission to the assets 102 and/or the output systems 108, among other examples.

The databases 406 may generally function to receive (e.g., from the data science system 404) and store data. As such, each database 406 may include one or more non-transitory computer-readable storage media, such as any of the examples provided above. In practice, the databases 406 may be separate from or integrated with the data storage 412.

The databases 406 may be configured to store numerous types of data, some of which is discussed below. In practice, some of the data stored in the databases 406 may include a timestamp indicating a date and time at which the data was generated or added to the database. Moreover, data may be stored in a number of manners in the databases 406. For instance, data may be stored in time sequence, in a tabular manner, and/or organized based on data source type (e.g., based on asset, asset type, sensor, or sensor type) or fault code, among other examples.

IV. Example Operations

The operations of the example network configuration 100 depicted in FIG. 1 will now be discussed in further detail below. To help describe some of these operations, flow diagrams may be referenced to describe combinations of operations that may be performed. In some cases, each block may represent a module or portion of program code that includes instructions that are executable by a processor to implement specific logical functions or steps in a process. The program code may be stored on any type of computer-readable medium, such as non-transitory computer-readable media. In other cases, each block may represent circuitry that is wired to perform specific logical functions or steps in a process. Moreover, the blocks shown in the flow diagrams may be rearranged into different orders, combined into fewer blocks, separated into additional blocks, and/or removed based upon the particular embodiment.

The following description may reference examples where a single data source, such as the asset 200, provides data to the analytics system 400 that then performs one or more functions. It should be understood that this is done merely for sake of clarity and explanation and is not meant to be limiting. In practice, the analytics system 400 generally receives data from multiple sources, perhaps simultaneously, and performs operations based on such aggregate received data.

A. Collection of Operating Data

As mentioned above, the representative asset 200 may take various forms and may be configured to perform a number of operations. In a non-limiting example, the asset 200 may take the form of a locomotive that is operable to transfer cargo across the United States. While in transit, the sensors 204 may obtain sensor data that reflects one or more operating conditions of the asset 200. The sensors 204 may transmit the sensor data to the processing unit 206.

The processing unit 206 may be configured to receive sensor data from the sensors 204. In practice, the processing unit 206 may receive sensor data from multiple sensors simultaneously or sequentially. As discussed above, while receiving the sensor data, the processing unit 206 may also be configured to determine whether sensor data satisfies sensor criteria that trigger any abnormal-condition indicators, such as fault codes. In the event the processing unit 206 determines that one or more abnormal-condition indicators are triggered, the processing unit 206 may be configured to perform one or more local operations, such as outputting an indication of the triggered indicator via a user interface 212.

The processing unit 206 may then be configured to transmit operating data for the asset 200 to the analytics system 400 via one of the network interfaces 210 and the communication network 104. For instance, the asset 200 may transmit operating data for to the analytics system 400 continuously, periodically, and/or in response to triggering events (e.g., fault codes). Specifically, the asset 200 may transmit operating data periodically based on a particular frequency (e.g., daily, hourly, every fifteen minutes, once per minute, once per second, etc.), or the asset 200 may be configured to transmit a continuous, real-time feed of operating data. Additionally or alternatively, the asset 200 may be configured to transmit operating data based on certain triggers, such as when sensor measurements from the sensors 204 satisfy sensor criteria for any abnormal-condition indicators. The asset 200 may transmit operating data in other manners as well.

In practice, operating data for the asset 200 may include sensor data and/or abnormal-condition data. In some implementations, the asset 200 may be configured to provide the operating data in a single data stream, while in other implementations the asset 200 may be configured to provide the operating data in multiple, distinct data streams. For example, the asset 200 may provide the analytics system 400 a first data stream of sensor data and a second data stream of abnormal-condition data. Other possibilities also exist.

Sensor data may take various forms. For example, at times, sensor data may include measurements obtained by each of the sensors 204. While at other times, sensor data may include measurements obtained by a subset of the sensors 204.

Specifically, the sensor data may include measurements obtained by the sensors associated with a given triggered abnormal-condition indicator. For example, if a triggered fault code is Fault Code 1 from FIG. 3, then the sensor data may include raw measurements obtained by Sensors A and C. Additionally or alternatively, the sensor data may include measurements obtained by one or more sensors not directly associated with the triggered fault code. Continuing off the last example, the sensor data may additionally include measurements obtained by Sensor B and/or other sensors. In some examples, the processing unit 206 may include particular sensor data in the operating data based on a fault-code rule or instruction provided by the analytics system 400, which may have, for example, determined that there is a correlation between that which Sensor B is measuring and that which caused the Fault Code 1 to be triggered in the first place. Other examples are also possible.

Further still, the sensor data may include one or more sensor measurements from each sensor of interest based on a particular time of interest, which may be selected based on a number of factors. In some examples, the particular time of interest may be based on a sampling rate. In other examples, the particular time of interest may be based on the time at which an abnormal-condition indicator is triggered.

In particular, based on the time at which an abnormal-condition indicator is triggered, the sensor data may include one or more respective sensor measurements from each sensor of interest (e.g., sensors directly and indirectly associated with the triggered fault code). The one or more sensor measurements may be based on a particular number of measurements or particular duration of time around the time of the triggered abnormal-condition indicator.

For example, if the triggered fault code is Fault Code 2 from FIG. 3, the sensors of interest might include Sensors B and C. The one or more sensor measurements may include the most recent respective measurements obtained by Sensors B and C prior to the triggering of the fault code (e.g., triggering measurements) or a respective set of measurements before, after, or about the triggering measurements. For example, a set of five measurements may include the five measurements before or after the triggering measurement (e.g., excluding the triggering measurement), the four measurements before or after the triggering measurement and the triggering measurement, or the two measurements before and the two after as well as the triggering measurement, among other possibilities.

Similar to sensor data, the abnormal-condition data may take various forms. In general, the abnormal-condition data may include or take the form of an indicator that is operable to uniquely identify a particular abnormal condition that occurred at the asset 200 from all other abnormal conditions that may occur at the asset 200. The abnormal-condition indicator may take the form of an alphabetic, numeric, or alphanumeric identifier, among other examples. Moreover, the abnormal-condition indicator may take the form of a string of words that is descriptive of the abnormal condition, such as "Overheated Engine" or "Out of Fuel", among other examples.

The analytics system 400, and in particular, the data intake system 402, may be configured to receive operating data from one or more assets and/or data sources, such as the asset 200. The data intake system 402 may be configured to perform one or more operations to the received data and then relay the data to the data science system 404. In turn, the data science system 404 may analyze the received data and based on such analysis, perform one or more operations.

B. Health Score

As one example, the data science system 404 may be configured to determine a "health score" for an asset, which is a single, aggregated metric that indicates whether a failure will occur at the asset within a given timeframe into the future (e.g., the next two weeks). In particular, in example implementations, a health score may indicate a likelihood that no failures from a group of failures will occur at the asset within a given timeframe into the future, or a health score may indicate a likelihood that at least one failure from a group of failures will occur at the asset within a given timeframe into the future.

In practice, depending on the desired granularity of the health metric, the data science system 404 may also be configured to determine different levels of health metrics. For example, the data science system 404 may determine a health metric for the asset as a whole (i.e., an asset-level health metric). As another example, the data science system 404 may determine a respective health metric for each of one or more subsystems of the asset (i.e., subsystem-level health metrics), which may also then be combined to generate an asset-level health metric. Other examples are also possible.

In general, determining a health metric may involve two phases: (1) a "modeling" phase during which the data science system 404 defines a model for predicting the likelihood of failures occurring and (2) an asset-monitoring phase during which the data science system 404 utilizes the model defined in the machine learning phase and operating data for a given asset to determine a health metric for the given asset.

Figure 5A:
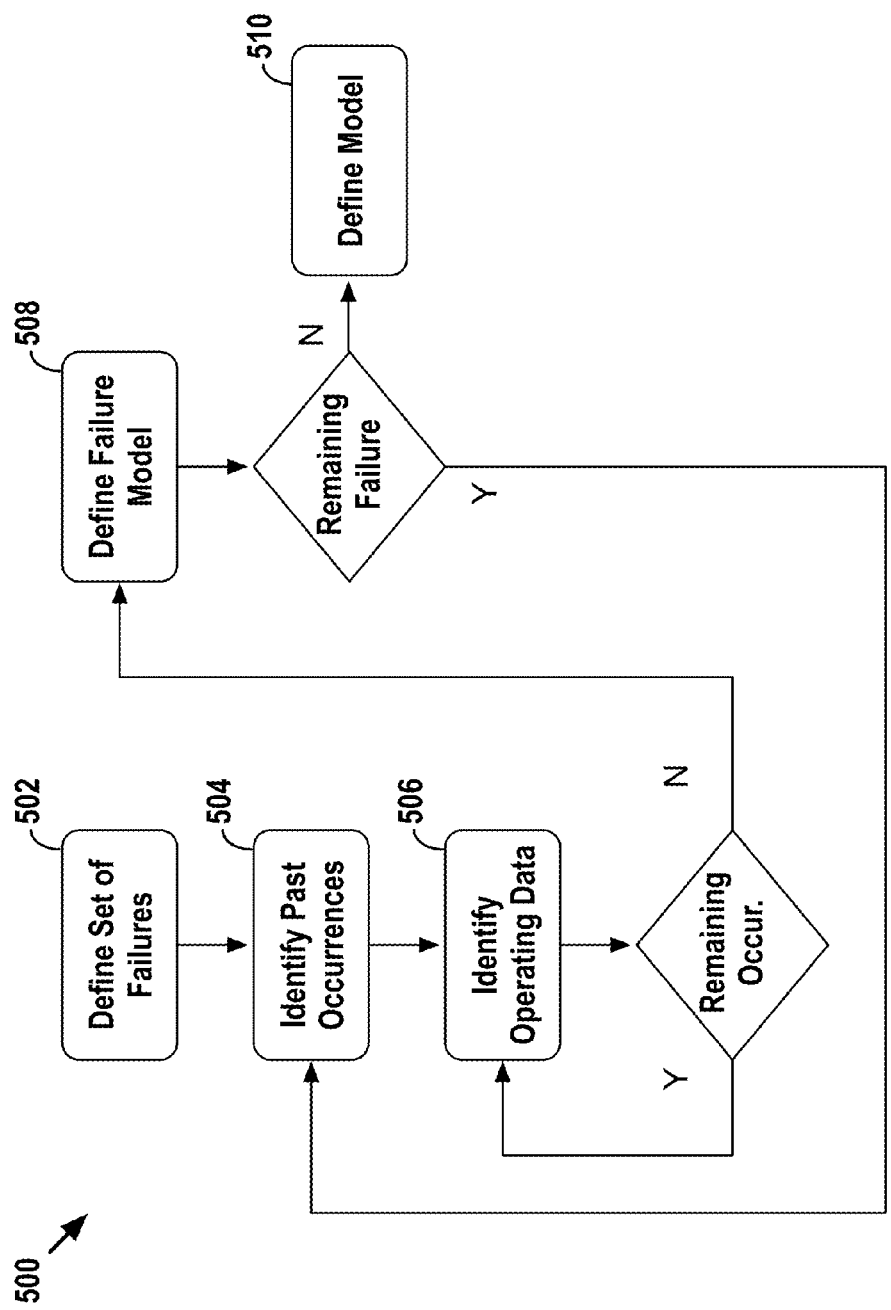
FIG. 5A depicts an example flow diagram of a modeling phase that may be used for determining a health metric.

FIG. 5A is a flow diagram 500 depicting one possible example of a modeling phase that may be used for determining a health metric. For purposes of illustration, the example modeling phase is described as being carried out by the data science system 404, but this modeling phase may be carried out by other systems as well. One of ordinary skill in the art will appreciate that the flow diagram 500 is provided for sake of clarity and explanation and that numerous other combinations of operations may be utilized to determine a health metric.

As shown in FIG. 5A, at block 502, the data science system 404 may begin by defining a set of the one or more failures that form the basis for the health metric (i.e., the failures of interest). In practice, the one or more failures may be those failures that could render an asset (or a subsystem thereof) inoperable if they were to occur. Based on the defined set of failures, the data science system 404 may take steps to define a model for predicting a likelihood of any of the failures occurring within a given timeframe in the future (e.g., the next two weeks).

In particular, at block 504, the data science system 404 may analyze historical operating data for a group of one or more assets to identify past occurrences of a given failure from the set of failures. At block 506, the data science system 404 may identify a respective set of operating data that is associated with each identified past occurrence of the given failure (e.g., sensor data from a given timeframe prior to the occurrence of the given failure). At block 508, the data science system 404 may analyze the identified sets of operating data associated with past occurrences of the given failure to define a relationship (e.g., a failure model) between (1) the values for a given set of operating metrics and (2) the likelihood of the given failure occurring within a given timeframe in the future (e.g., the next two weeks). Lastly, at block 510, the defined relationship for each failure in the defined set (e.g., the individual failure models) may then be combined into a model for predicting the overall likelihood of a failure occurring.

As the data science system 404 continues to receive updated operating data for the group of one or more assets, the data science system 404 may also continue to refine the predictive model for the defined set of one or more failures by repeating steps 504-510 on the updated operating data.

The functions of the example modeling phase illustrated in FIG. 5A will now be described in further detail. Starting with block 502, as noted above, the data science system 404 may begin by defining a set of the one or more failures that form the basis for the health metric. The data science system 404 may perform this function in various manners.

In one example, the set of the one or more failures may be based on one or more user inputs. Specifically, the data science system 404 may receive from a computing system operated by a user, such as an output system 108, input data indicating a user selection of the one or more failures. As such, the set of one or more failures may be user defined.

In other examples, the set of the one or more failures may be based on a determination made by the data science system 404. In particular, the data science system 404 may be configured to define the set of one or more failures, which may occur in a number of manners.

For instance, the data science system 404 may be configured to define the set of failures based on one or more characteristics of the asset 200. That is, certain failures may correspond to certain characteristics, such as asset type, class, etc., of an asset. For example, each type and/or class of asset may have respective failures of interest.

In another instance, the data science system 404 may be configured to define the set of failures based on historical data stored in the databases 406 and/or external data provided by the data sources 110. For example, the data science system 404 may utilize such data to determine which failures result in the longest repair-time and/or which failures are historically followed by additional failures, among other examples.

In yet other examples, the set of one or more failures may be defined based on a combination of user inputs and determinations made by the data science system 404. Other examples are also possible.

At block 504, for each of the failures from the set of failures, the data science system 404 may analyze historical operating data for a group of one or more assets (e.g., fault code data) to identify past occurrences of a given failure. The group of the one or more assets may include a single asset, such as asset 200, or multiple assets of a same or similar type, such as fleet of assets. The data science system 404 may analyze a particular amount of historical operating data, such as a certain amount of time's worth of data (e.g., a month's worth) or a certain number of data-points (e.g., the most recent thousand data-points), among other examples.

In practice, identifying past occurrences of the given failure may involve the data science system 404 identifying the type of operating data, such as abnormal-condition data, that indicates the given failure. In general, a given failure may be associated with one or multiple abnormal-condition indicators, such as fault codes. That is, when the given failure occurs, one or multiple abnormal-condition indicators may be triggered. As such, abnormal-condition indicators may be reflective of an underlying symptom of a given failure.

After identifying the type of operating data that indicates the given failure, the data science system 404 may identify the past occurrences of the given failure in a number of manners. For instance, the data science system 404 may locate, from historical operating data stored in the databases 406, abnormal-condition data corresponding to the indicators associated with the given failure. Each located abnormal-condition data would indicate an occurrence of the given failure. Based on this located abnormal-condition data, the data science system 404 may identify a time at which a past failure occurred.

At block 506, the data science system 404 may identify a respective set of operating data that is associated with each identified past occurrence of the given failure. In particular, the data science system 404 may identify a set of sensor data from a certain timeframe around the time of the given occurrence of the given failure. For example, the set of data may be from a particular timeframe (e.g., two weeks) before, after, or around the given occurrence of the failure. In other cases, the set of data may be identified from a certain number of data-points before, after, or around the given occurrence of the failure.

In example implementations, the set of operating data may include sensor data from some or all of the sensors 204. For example, the set of operating data may include sensor data from sensors associated with a fault code corresponding to the given failure.

Figure 6:
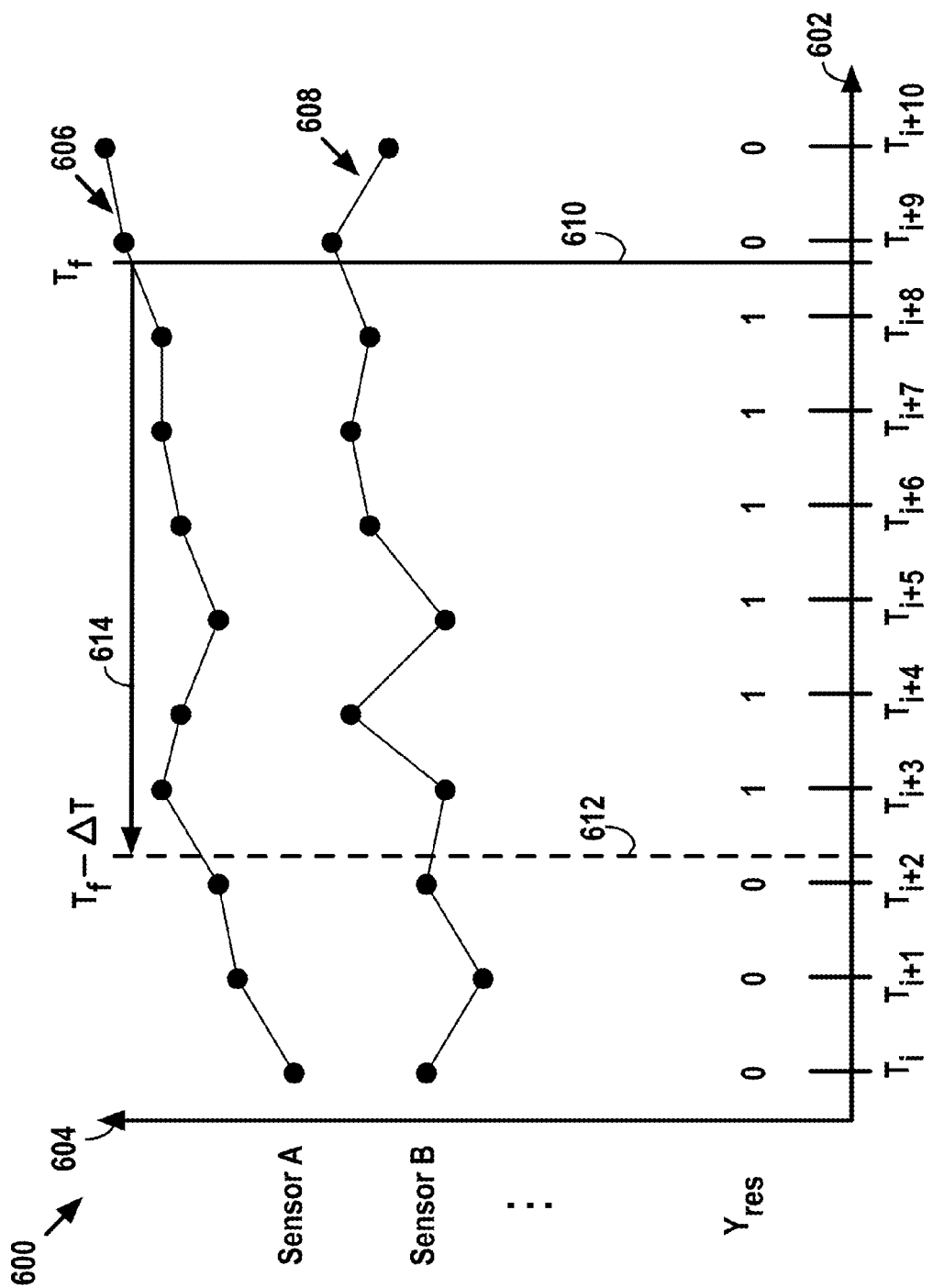
FIG. 6 depicts a conceptual illustration of data utilized to define a model.

To illustrate, FIG. 6 depicts a conceptual illustration of historical operating data that the data science system 404 may analyze to facilitate defining a model. Plot 600 may correspond to a segment of historical sensor data that originated from some (e.g., Sensor A and Sensor B) or all of the sensors 204. As shown, the plot 600 includes time on the x-axis 602, sensor measurement values on the y-axis 604, and sensor data 606 corresponding to Sensor A and sensor data 608 corresponding to Sensor B, each of which includes various data-points representing sensor measurements at particular points in time, $T_i$. Moreover, the plot 600 includes an indication of an occurrence of a failure 610 that occurred at a past time, $T_f$ (e.g., "time of failure"), and an indication of an amount of time 612 before the occurrence of the failure, $\Delta T$, from which sets of operating data are identified. As such, $T_f$-$\Delta T$ defines a timeframe 614 of data-points of interest.

Returning to FIG. 5A, after the data science system 404 identifies the set of operating data for the given occurrence of the given failure (e.g., the occurrence at $T_f$), the data science system 404 may determine whether there are any remaining occurrences for which a set of operating data should be identified. In the event that there is a remaining occurrence, block 506 would be repeated for each remaining occurrence.

Thereafter, at block 508, the data science system 404 may analyze the identified sets of operating data associated with the past occurrences of the given failure to define a relationship (e.g., a failure model) between (1) a given set of operating metrics (e.g., a given set of sensor measurements) and (2) the likelihood of the given failure occurring within a given timeframe in the future (e.g., the next two weeks). That is, a given failure model may take as inputs sensor measurements from one or more sensors and output a probability that the given failure will occur within the given timeframe in the future.

In general, a failure model may define a relationship between operating conditions of the asset 200 and the likelihood of a failure occurring. In some implementations, in addition to raw data signals from sensors 204, a failure model may receive a number of other data inputs, also known as features, which are derived from the sensor signals. Such features may include an average or range of sensor values that were historically measured when a failure occurred, an average or range of sensor-value gradients (e.g., a rate of change in sensor measurements) that were historically measured prior to an occurrence of a failure, a duration of time between failures (e.g., an amount of time or number of data-points between a first occurrence of a failure and a second occurrence of a failure), and/or one or more failure patterns indicating sensor measurement trends around the occurrence of a failure. One of ordinary skill in the art will appreciate that these are but a few example features that can be derived from sensor signals and that numerous other features are possible.

In practice, a failure model may be defined in a number of manners. In example implementations, the data science system 404 may define a failure model by utilizing one or more modeling techniques that return a probability between zero and one, such as a random forest technique, logistic regression technique, or other regression technique.

In a particular example, defining a failure model may involve the data science system 404 generating a response variable based on the historical operating data identified at block 506. Specifically, the data science system 404 may determine an associated response variable for each set of sensor measurements received at a particular point in time. As such, the response variable may take the form of a data set associated with the failure model.

The response variable may indicate whether the given set of sensor measurements is within any of the timeframes determined at block 506. That is, a response variable may reflect whether a given set of sensor data is from a time of interest about the occurrence of a failure. The response variable may be a binary-valued response variable such that if the given set of sensor measurements is within any of determined timeframes, the associated response variable is assigned a value of one, and otherwise, the associated response variable is assigned a value of zero.

Returning to FIG. 6, a conceptual illustration of a response variable vector, $Y_{res}$ is shown on the plot 600. As shown, response variables associated with sets of sensor measurements that are within the timeframe 614 have a value of one (e.g., $Y_{res}$ at times $T_{i+3}$-$T_{i+8}$), while response variables associated with sets of sensor measurements outside the timeframe 614 have a value of zero (e.g., $Y_{res}$ at times $T_i$-$T_{i+2}$ and $T_{i+9}$-$T_{i+10}$). Other response variables are also possible.

Continuing in the particular example of defining a failure model based on a response variable, the data science system 404 may train the failure model with the historical operating data identified at block 506 and the generated response variable. Based on this training process, the data science system 404 may then define the failure model that receives as inputs various sensor data and outputs a probability between zero and one that a failure will occur within a period of time equivalent to the timeframe used to generate the response variable.

In some cases, training with the historical operating data identified at block 506 and the generated response variable may result in variable importance statistics for each sensor. A given variable importance statistic may indicate the sensor's relative effect on the probability that a given failure will occur within the period of time into the future.

Additionally or alternatively, the data science system 404 may be configured to define a failure model based on one or more survival analysis techniques, such as a Cox proportional hazard technique. The data science system 404 may utilize a survival analysis technique similarly in some respects to the above-discussed modeling technique, but the data science system 404 may determine a survival time-response variable that indicates an amount of time from the last failure to a next expected event. A next expected event may be either reception of sensor measurements or an occurrence of a failure, whichever occurs first. This response variable may include a pair of values that are associated with each of the particular points in time at which sensor measurements are received. The response variable may then be utilized to determine a probability that a failure will occur within the given timeframe in the future.

In some example implementations, a failure model may be defined based in part on external data, such as weather data and/or "hot box" data, among other data. For instance, based on such data, the failure model may increase or decrease an output failure probability.

In practice, external data may be observed at points in time that do not coincide with times at which the sensors 204 obtain measurements. For example, the times at which "hot box" data is collected (e.g., times at which a locomotive passes along a section of railroad track that is outfitted with hot box sensors) may be in disagreement with sensor measurement times. In such cases, the data science system 404 may be configured to perform one or more operations to determine external data observations that would have been observed at times that correspond to the sensor measurement times.

Specifically, the data science system 404 may utilize the times of the external data observations and times of the sensor measurements to interpolate the external data observations to produce external data values for times corresponding to the sensor measurement times. Interpolation of the external data may allow external data observations or features derived therefrom to be included as inputs into the failure model. In practice, various techniques may be used to interpolate the external data with the sensor data, such as nearest-neighbor interpolation, linear interpolation, polynomial interpolation, and spline interpolation, among other examples.

Returning to FIG. 5A, after the data science system 404 determines a failure model for a given failure from the set of failures defined at block 502, the data science system 404 may determine whether there are any remaining failures for which a failure model should be determined. In the event that there remains a failure for which a failure model should be determined, the data science system 404 may repeat the loop of blocks 504-508. In some implementations, the data science system 404 may determine a single failure model that encompasses all of the failures defined at block 502. In other implementations, the data science system 404 may determine a failure model for each subsystem of an asset, which may then be utilized to determine an asset-level failure model (see below for further discussion). Other examples are also possible.

Lastly, at block 510, the defined relationship for each failure in the defined set (e.g., the individual failure models) may then be combined into the model (e.g., the health-metric model) for predicting the overall likelihood of a failure occurring within the given timeframe in the future (e.g., the next two weeks). That is, the model receives as inputs sensor measurements from one or more sensors and outputs a single probability that at least one failure from the set of failures will occur within the given timeframe in the future.

The data science system 404 may define the health-metric model in a number of manners, which may depend on the desired granularity of the health metric. That is, in instances where there are multiple failure models, the outcomes of the failure models may be utilized in a number of manners to obtain the output of the health-metric model. For example, the data science system 404 may determine a maximum, median, or average from the multiple failure models and utilize that determined value as the output of the health-metric model.

In other examples, determining the health-metric model may involve the data science system 404 attributing a weight to individual probabilities output by the individual failure models. For instance, each failure from the set of failures may be considered equally undesirable, and so each probability may likewise be weighted the same in determining the health-metric model. In other instances, some failures may be considered more undesirable than others (e.g., more catastrophic or require longer repair time, etc.), and so those corresponding probabilities may be weighted more than others.

In yet other examples, determining the health-metric model may involve the data science system 404 utilizing one or more modeling techniques, such as a regression technique. In particular, the data science system 404 may regress on the probabilities output by the individual failure models and an aggregate response variable. An aggregate response variable may take the form of the logical disjunction (logical OR) of the response variables (e.g., $Y_{res}$ in FIG. 6) from each of the individual failure models. For example, aggregate response variables associated with any set of sensor measurements that occur within any timeframe determined at block 506 (e.g., the timeframe 614 of FIG. 6) may have a value of one, while aggregate response variables associated with sets of sensor measurements that occur outside any of the timeframes may have a value of zero. Other manners of defining the health-metric model are also possible.

In some implementations, block 510 may be unnecessary. For example, as discussed above, the data science system 404 may determine a single failure model, in which case the health-metric model may be the single failure model.

In practice, the data science system 404 may be configured to update the individual failure models and/or the overall health-metric model. The data science system 404 may update a model daily, weekly, monthly, etc. and may do so based on a new portion of historical operating data from the asset 200 or from other assets (e.g., from other assets in the same fleet as the asset 200). Other examples are also possible.

Figure 5B:
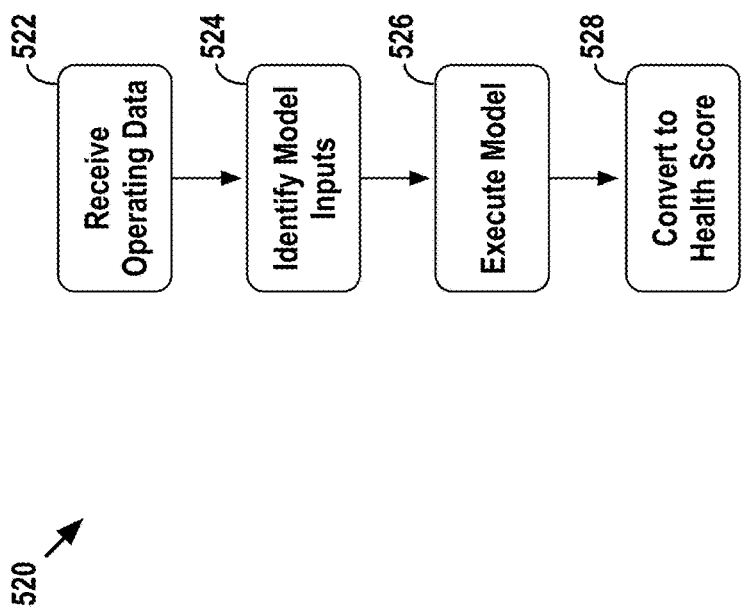
FIG. 5B depicts an example flow diagram of an asset-monitoring phase that may be used for determining a health score.

FIG. 5B is next a flow diagram 520 depicting one possible example of an asset-monitoring phase that may be used for determining a health metric. For purposes of illustration, the example asset-monitoring phase is described as being carried out by the data science system 404, but this asset-monitoring phase may be carried out by other systems as well. One of ordinary skill in the art will appreciate that the flow diagram 520 is provided for sake of clarity and explanation and that numerous other combinations of operations and functions may be utilized to determine a health metric.

As shown in FIG. 5B, at block 522, the data science system 404 may receive data that reflects the current operating conditions of a given asset. At block 524, the data science system 404 may identify, from the received data, the set of operating data that is to be input into the model defined during the modeling phase. At block 526, the data science system 404 may then input the identified set of operating data into the model, which in turn determines and outputs an overall likelihood of a failure occurring within the given timeframe in the future (e.g., the next two weeks). Lastly, at block 528, the data science system 404 may convert this likelihood into the health metric.

As the data science system 404 continues to receive updated operating data for the given asset, the data science system 404 may also continue to update the health metric for the given asset by repeating the operations of blocks 522-528 based on the updated operating data. In some cases, the operations of blocks 522-528 may be repeated each time the data science system 404 receives new data or periodically (e.g., daily, weekly, monthly, etc.). In this way, the analytics system 400 may be configured to dynamically update health metrics, perhaps in real-time, as assets are used in operation.

The functions of the example "asset-monitoring" phase illustrated in FIG. 5B will now be described in further detail. At block 522, the data science system 404 may receive data that reflects the current operating conditions of a given asset. In particular, the data intake system 402 may receive operating data for the asset 200, which is then passed to the data science system 404. In example implementations, the operating data may include at least sensor data from one or more of the sensors 204 but no abnormal-condition data. In other implementations, the operating data may include both. In some examples, the data science system 404 may also receive from data sources 110 external data associated with the present operation of the asset 200.

At block 524, the data science system 404 may identify, from the received data, the set of operating data that is to be input into the health-metric model defined during the modeling phase. This operation may be performed in a number of manners.

In one example, the data science system 404 may identify the set of operating data inputs (e.g., sensor data from particular sensors of interest) for the model based on a characteristic of the given asset, such as asset type or asset class, for which the health metric is being determined. In some cases, the identified set of operating data inputs may be sensor data from some or all of the sensors of the given asset.

In another example, the data science system 404 may identify the set of operating data inputs for the model based on the defined set of failures from block 502 of FIG. 5A. Specifically, the data science system 404 may identify all the abnormal-condition indicators that are associated with the failures from the set of failures. For each of these identified indicators, the data science system 404 may identify the sensors associated with a given indicator. The data science system 404 may set the operating data inputs to include sensor data from each of the identified sensors. Other examples of identifying the set of operating data inputs are also possible.

At block 526, the data science system 404 may then execute the health-metric model. Specifically, the data science system 404 may input the identified set of operating data into the model, which in turn determines and outputs an overall likelihood of at least one failure occurring within the given timeframe in the future (e.g., the next two weeks).

In some implementations, this operation may involve the data science system 404 inputting particular operating data (e.g., sensor data) into the one or more failure models defined at block 508 of FIG. 5A, which each may output an individual probability. The data science system 404 may then use these individual probabilities, perhaps weighting some more than others in accordance with the health-metric model, to determine the overall likelihood of a failure occurring within the given timeframe in the future.

Lastly, at block 528, the data science system 404 may convert the probability of a failure occurring into the health score that may take the form of a single, aggregated parameter that reflects the likelihood that no failures will occur at the asset within the give timeframe in the future (e.g., two weeks). In example implementations, converting the failure probability into the health metric may involve the data science system 404 determining the complement of the failure probability. Specifically, the overall failure probability may take the form of a value ranging from zero to one; the health metric may be determined by subtracting one by that number. Other examples of converting the failure probability into the health metric are also possible.

C. Output of Asset Information

In another aspect, the analytics system 400 may further be configured to facilitate causing one or more of the output systems 108 to output various information regarding an asset in operation, such as an indication of the health metric and perhaps an indication of fault codes and/or sensor data as well. These indications may take various forms.

Figure 7:
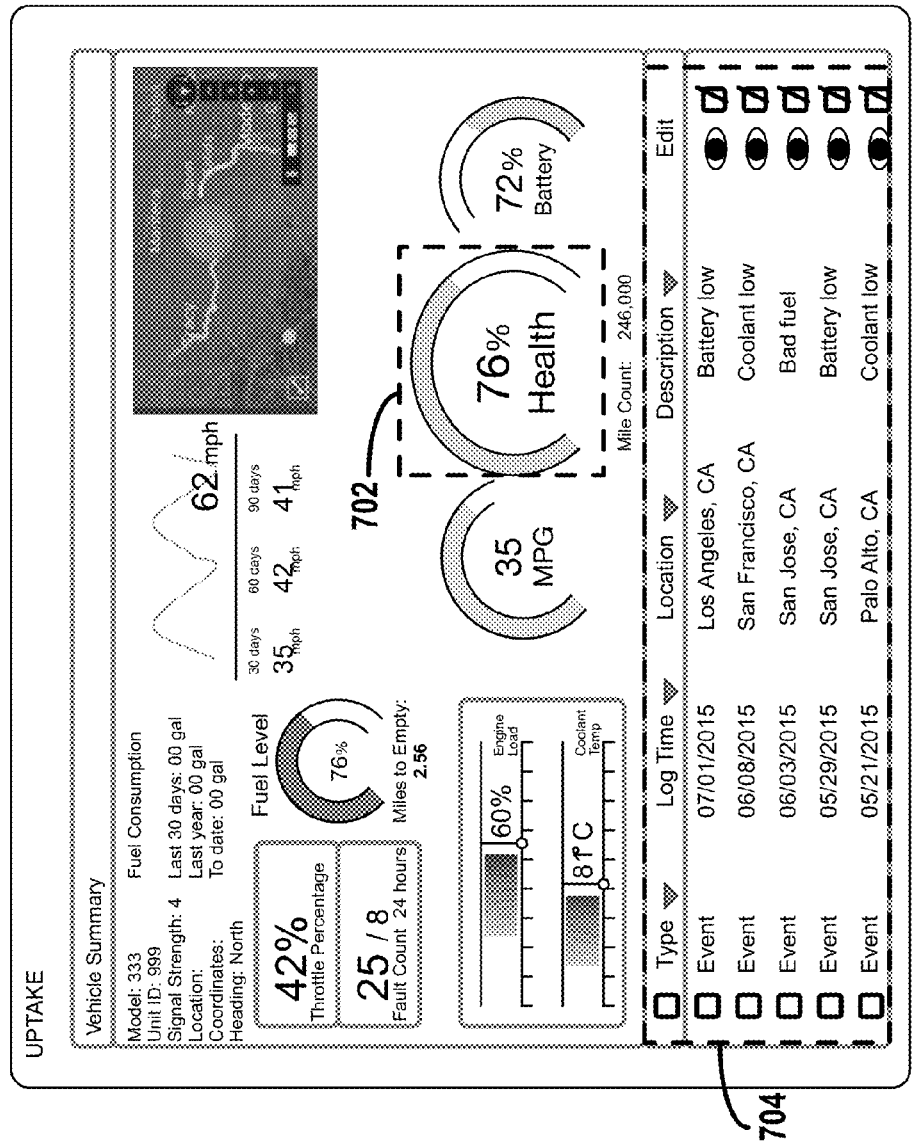
FIG. 7 depicts an example graphical user interface showing a representation of a health score.

FIG. 7 depicts an example graphical user interface 700 that may be displayed by an output system 108 in accordance with instructions from the analytics system 400. This graphical user interface 700 is shown to include various information about a given asset (e.g., a vehicle asset). For example, as shown, the graphical user interface 700 may include a health-metric display 702 that shows the asset's overall health metric (outlined by the dashed, black box). Here, the health-metric display 702 takes the form of a percentage and a dial-like visualization, but this display may take various other forms as well.

Further, as shown, the graphical user interface 700 may include an event log 704 that shows information related to abnormal-condition indicators triggered at the given asset. This event log 704 may include various information regarding the indicators, such as the time that a given indicator was triggered, the location of the asset when the indicator was triggered, and a brief description associated with the indicator. The event log 704 may also include a selectable element for each indicator that, once selected, may cause the graphical user interface 700 to display an indication of the sensor data that contributed to triggering the abnormal-condition indicator. Moreover, as shown, the graphical user interface 700 may include other information related to the given asset, such as the asset's current location and various key performance indicators. Various other example graphical user interfaces are possible as well.

D. Triggering Actions Based on Health Score

As another aspect, the analytics system 400 may be configured to use a health metric to trigger one or more actions that may help modify the health metric of the asset 200. In some cases, if the health metric falls below a particular threshold value, an action may be triggered that may facilitate increasing the health metric of the asset 200. Such actions may be referred to herein as "preventative actions" in that these actions aim to help prevent a failure from occurring.

In particular, the data science system 404 may be configured to monitor the health metric generated for the asset 200 and determine whether the health metric reaches a threshold value, which may have been predetermined and stored in a database 406 or dynamically determined by the data science system 404. Various actions are possible in the event that the health metric does fall below the threshold.

For example, the analytics system 400 may be configured to cause an output system 108 to display a warning or alert. For instance, the warning or alert may include a visual, audible, or combination thereof indication of the decreasing health metric. In a particular case, the analytics system 400 may case the output system 108 to display animated visualizations, such as flashing or growing visualizations, and/or output an alarm sound or the like.

In another example, based on the health metric reaching a threshold value, the analytics system 400 may generate a list of one or more recommended actions that may help increase the health metric. For instance, a recommended action may be to repair a particular subsystem of the asset 200, to operate the asset 200 according to certain operating conditions, or to steer the asset 200 around a particular geographical region, among other examples. The analytics system 400 may then cause an output system 108 to output an indication of the recommended actions.

In other examples, based on the health metric reaching a threshold value, the analytics system 400 may be configured to cause a work-order system to generate a work order to repair the asset 200. In particular, the analytics system 400 may transmit work-order data to a work-order system that causes the work-order system to output a work order, which may specify a certain repair that may help increase the health metric. Similarly, the analytics system 400 may be configured to transmit part-order data to cause a parts-ordering system to order a particular part for the asset 200 that may be needed in the repair of the asset 200. Other possibilities also exist.

In yet other examples, based on the health metric reaching a threshold value, the analytics system 400 may be configured to transmit to the asset 200 one or more commands that facilitate modifying one or more operating conditions of the asset 200. For instance, a command may cause the asset 200 to decrease (or increase) velocity, acceleration, fan speed, propeller angle, and/or air intake, among other examples. Other actions are also possible.

E. Subsystem Health Metrics

As suggested above, in some implementations, the analytics system 400 may be configured to determine one or more subsystem-level health metric. Specifically, the analytics system 400 may be configured to determine a subsystem-level health metric as a standalone health metric and/or multiple subsystem-level health metrics that may be utilized to determine an asset-level health metric. A given subsystem health metric may indicate a single, aggregated parameter that reflects whether a failure will occur at the particular subsystem of the given asset within a certain period of time into the future.

Generally, a subsystem-level health metric may be determined in a manner similar, at least in some respects, to the operations discussed with reference to FIGS. 5A and 5B. However, some of the operations may be modified, or are perhaps unnecessary, in determining a subsystem-level health metric or additional operations may be utilized.

In particular, in some implementations, at block 502, the set of failures may include failures that could render the particular subsystem inoperable if they were to occur. In some cases, the set of failures may be defined from abnormal-condition indicators, such as fault codes, associated with a subsystem. In general, a subsystem may have one or multiple indicators associated with it. For example, Fault Codes 1-3 of FIG. 3 may all be associated with a given subsystem 202. The data science system 404 may determine the indicators associated with the given subsystem 202 in a number of manners.

In some examples, the abnormal-condition indicators associated with the given subsystem 202 may be user defined. In particular, the data science system 404 may receive an indication of the given subsystem 202 and indicators associated with the given subsystem 202, perhaps from an output system 108 that received inputs from a user.

In other examples, the data science system 404 may be configured to determine the abnormal-condition indicators associated with the given subsystem 202. This operation may be based on historical data stored in the databases 406 and/or external data provided by the data sources 110.

For instance, historical repair data may be utilized. Based on such data, the data science system 404 may be configured to determine instances when the given subsystem 202 was repaired (e.g., a time and/or date of the repair). Based on that determination, the data science system 404 may then determine from the historical operating data any abnormal-condition indicators that were triggered before the repair. In other examples, the data science system 404 may instead determine from the historical operating data only those abnormal-condition indicators that were triggered before and then no longer triggered after the repair. In any event, the determined indicators may then be associated with the given subsystem 202.

In yet another example, the data science system 404 may be configured to determine abnormal-condition indicators associated with the given subsystem 202 by determining relevant sensors, which are sensors associated with the given subsystem 202, and then determining indicators associated with the relevant sensors. In some cases, the data science system 404 may determine the relevant sensors based on sensor attributes, such as sensor location on the asset 200 and/or sensor type (e.g., the physical property the sensor is configured to measure). For example, the data science system 404 may be configured to determine sensors that are physically located on or within the given subsystem 202. Additionally or alternatively, the data science system 404 may be configured to determine sensors that are in proximity to the given subsystem 202, such as sensors downstream or upstream of the given subsystem 202.

Further, the data science system 404 may be configured to determine sensors that are located on or within subsystems that affect the operation of the given subsystem 202. For instance, the data science system 404 may be configured to determine subsystems from which the given subsystem 202 receives inputs and/or subsystems to which the given subsystem 202 provides outputs. Or subsystems whose operating conditions are modified by the given subsystem 202 and/or subsystems that modify the operating conditions of the given subsystem 202. For example, the data science system 404 may determine that the sensors on an air-intake subsystem that operates to reduce operating temperatures of an engine subsystem are relevant to the engine subsystem.

In any event, after the data science system 404 determines the relevant sensors, the data science system 404 may be configured to determine any abnormal-condition indicators whose sensor criteria include measurements from the relevant sensors. These determined indicators then would be associated with the given subsystem 202 and used to identify the past occurrences of failures at block 504.

Another example operation that may differ in some respects to the subsystem-level health metric context is with respect to block 510. In particular, when determining an asset-level health metric from multiple subsystem-level health metrics, the data science system 404 may be configured to combine the multiple health metrics in a number of manners, some of which may be similar in some respects to the methods of combining failure models discussed above. In some implementations, the data science system 404 may be configured to weight each subsystem health metric equally or to weight certain subsystem-level health metrics different than others, which may be based on the subsystem.

The weighting may be based on the relative importance of a subsystem relative to the overall operation of the asset. For example, Subsystem A might have a health metric of 75% and Subsystem B might have a health metric of 85%. Weighting each subsystem health metric equally in determining an asset-level health metric might result in a health metric of 80%. On the other hand, assuming Subsystem A is determined to be three times more important than Subsystem B, weighting each subsystem health metric according to the subsystems' relative importance might result in a health metric of 77.5%. Other examples are also possible.

In any event, similar to the asset-level health metrics, the analytics system 400 may be configured to trigger a number of actions based on a subsystem health metric. However, the triggered actions may be more granular than those triggered based on an asset-level health metric. In particular, any of the actions discussed above may be directed to the given subsystem or a component thereof.

Moreover, subsystem-level health metrics may allow the analytics system 400 to more quickly identify sensor measurements that suggest a failure might occur in the future. Accordingly, when determining a subsystem-level health metric, the analytics system 400 might be configured to forecast for a smaller window of time than in the asset-level health metrics, thereby providing a more useful prediction. For instance, while an asset-level health metric might have a resolution of a first amount of time with a particular degree of accuracy (e.g., the asset-level health metric may indicate a probability that no faults will occur in the next two weeks), a subsystem-level health metric may have a resolution of a second, smaller amount of time with the same degree of accuracy (e.g., the subsystem-level health metric may indicate a probability that no faults will occur in the next week). Other advantages of subsystem-level health metrics are also possible.

F. Updating Health Metric Module Based on Feedback

In another aspect, the analytics system 400 may be configured to receive feedback data regarding an action triggered based on a health metric, and then based on the feedback data, update the health-metric model and/or actions triggered based on health metrics (collectively referred to herein as the "health metric module").

This feedback data may take various forms, but in general, the feedback data may indicate a status of an action triggered based on health metric data. Examples of this status may be that the action was acted upon, that the action was performed and successfully corrected an impending failure, that the action was performed but did not correct an issue, or that the action was not feasible, among other examples. Further, the analytics system 400 may receive this feedback data from various sources, examples of which include a user operated output device or system.

In a particular example, based on a health metric, the analytics system 400 may have triggered generating a work order to repair a particular component of a given asset. After completing the work order, the mechanic may utilize a client device of an output system 108 to provide feedback regarding the actions taken in response to the work order, such as an indication that the particular component indeed needed to be fixed and/or that the repair was performed successfully or that the particular component did not need to be fixed and/or the repair could not be performed. The analytics system 400 may receive this feedback data and then use it to update the health metric module in various manners.

For instance, the analytics system 400 could refine the health metric module based on this feedback data. Specifically, the feedback data may cause the analytics system 400 to add or remove a failure to or from the set of failures from block 502 of FIG. 5A, modify a weight applied to an output of a given failure model, and/or adjust a particular predictive algorithm utilized to predict a likelihood of a given failure occurring, among other examples. In another instance, the analytics system 400 may update the health metric module so as to prioritize a type of action over others if the health metric falls below a health threshold in the future. Many other examples are possible as well.

In another example of feedback data, the analytics system 400 may have caused an output system 108 to display an indication of a list of recommended routes for a given asset to take that may help increase (or at least maintain) the health metric (e.g., routes with few elevation changes and/or climbs). Thereafter, the analytics system 400 may receive feedback data indicating that a recommended route is not feasible because of construction on the route. Based on such feedback, the analytics system 400 may remove the recommended route from the list of recommended routes. Other examples are also possible.

G. Improving Handling of Indicators

The analytics system 400 may be configured to receive other forms of feedback data and perform other operations as well. For example, the analytics system 400 may be configured to intelligently suppress abnormal-condition indicators, such as fault codes that, would typically be generated and displayed to a user.

As discussed above, some traditional asset-monitoring systems generate abnormal-condition indicators for "false positives", which are indicators that are not meaningful to a user because the underlying faults do not impact the overall operation of an asset. Examples of such faults may include a broken windshield wiper, low windshield wiper fluid, a broken anemometer, and a burned out instrumentation panel light, among other examples. Such "false positive" indicators may distract users from meaningful indicators or may desensitize a user's reaction to receiving indications of abnormal conditions. To help resolve some of these issues, the analytics system 400 may be configured to adapt to responses to particular abnormal-condition indicators and intelligently respond to operating conditions that traditionally result in the analytics system 400 automatically generating an abnormal-condition indicator.

For sake of clarity, the operations and functions involved with adaptively handling operating conditions that typically trigger abnormal-condition indicators are discussed in the context of fault codes. However, some or all of these operations and functions may be implemented in other contexts with various other types of abnormal-condition indicators.

In operation, the analytics system 400 may be configured to facilitate causing an output system 108 to display an indication of a given fault code. The analytics system 400 may do so in a number of manners.

In one example, the analytics system 400 may facilitate causing an output system 108 to display an indication of a given fault code based on sensor data from an asset. In particular, the analytics system 400 may receive from the asset 200 sensor data that the analytics system 400 analyzes. If the received sensor data satisfies sensor criteria, perhaps stored in a database 406, the analytics system 400 may transmit fault code data to the output system 108 to cause the output system 108 to display an indication of the given fault code.

In another example, the analytics system 400 may facilitate causing an output system 108 to display an indication of a given fault code based on fault code data from an asset. Specifically, the analytics system 400 may receive from the asset 200 fault code data indicating a given fault, and the analytics system 400 may then relay the fault code data to the output system 108. In some cases, the analytics system 400 may have facilitated the asset 200 generating the fault code data in the first place. For instance, the analytics system 400 could be configured to generate fault-code rules, which identify one or more sensors and corresponding sensor criteria that trigger the given fault code, that the analytics system 400 transmits to the asset 200 to facilitate causing the asset 200 to trigger fault codes.

In any event, the output system 108 may output an indication of the given fault code. The indication of the given fault code may take various forms, such as visual, audible, or some combination thereof. In some cases, the output system 108 displays a fault code to a user and provides the user options with regard to the alert. For example, the options may allow the user to dismiss the fault code (e.g., by selecting a "Disregard" icon or the like), to take action on the fault code (e.g., by selecting a "Resolve" icon or the like), or to ignore the fault code (e.g., by making no selection for a predetermined amount of time), among other possible options.

Figure 8A:
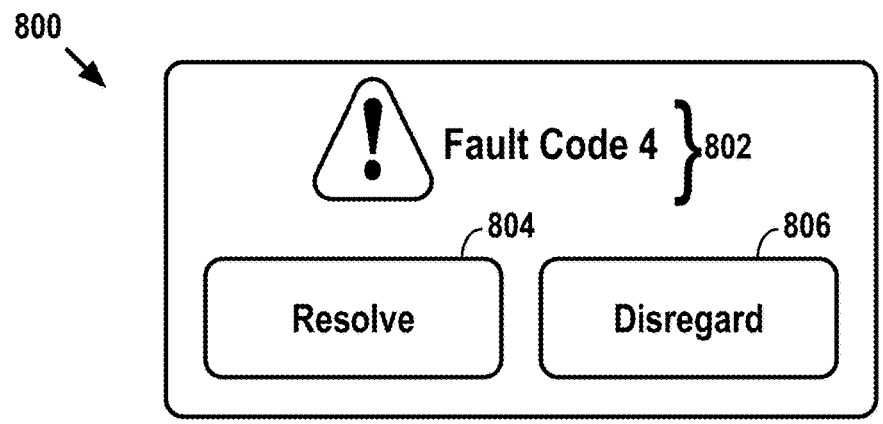
FIG. 8A depicts an example visual indication of an abnormal-condition indicator.

FIG. 8A depicts an example visual indication 800 of a given fault code. The output system 108 may display the visual indication 800 in response to receiving fault code data from the analytics system 400. As shown, the visual indication 800 includes a fault alert 802 identifying the triggered fault code (e.g., Fault Code 4), an action icon 804, and a dismiss icon 806. In operation, a user may select the action icon 804 to obtain a list of recommended actions that may be performed to try to fix the cause of the fault alert 802. On the other hand, a user may select the dismiss icon 806 to disregard the fault alert 802, and once selected, the visual indication 800 may disappear.

In practice, the user reviewing and making a decision regarding the fault codes may be a number of persons. In some examples, a human manager who is responsible for the oversight of multiple assets may review the fault codes (e.g., remotely via a computing system communicating with the analytics system 300). The human manager may have expert knowledge regarding how certain fault codes should be handled. In some examples, multiple users may review the same fault codes.

The analytics system 400 may be configured to receive feedback data that is indicative of the user's decision regarding the outputted fault code. Specifically, the output system 108 operated by the user may provide the feedback data. The feedback data may take various forms.

In some examples, the feedback data may explicitly indicate the user's decision (e.g., data indicating the user selected the dismiss icon 806). In other examples, the analytics system 400 may be configured to infer the user's decision from the feedback data.

In particular, the analytics system 400 may be configured to infer a decision based on operating data received from the asset 200 after transmitting the fault code data. For instance, the analytics system 400 may be configured to infer that a user decided to take action if the operating data changes such that the fault code is no longer triggered. On the other hand, the analytics system 400 may be configured to infer that the user decided to dismiss or ignore the fault code if the fault code persists (e.g., operating data continues to include fault code data indicating the given fault code and/or sensor data satisfying sensor criteria associated with the fault code) for a certain amount of time, such as one or more hours, days, or weeks, after transmitting the fault code data. Other examples of inferring a user's decisions are also possible.

In any event, the analytics system 400 may be configured to aggregate feedback data over time and store such data in the database 406. The analytics system 400 may be configured to aggregate feedback data corresponding to one or more users reviewing fault codes. Moreover, the aggregated feedback data may correspond to fault code decisions for the asset 200 and/or for other assets.

Based on the historical feedback data, the analytics system 400 may be configured to determine a response pattern for each fault code and store such patterns in the database 406. A response pattern may reflect how often a particular response is utilized with the given fault code.

A response pattern may be determined in a number of manners. In one example, the response pattern may be determined from response counters corresponding to each possible response to a given fault code. The response counters may be incremented each time a particular response is identified for an instance of the given fault code. From such counters, the response patterns may be determined.

In any event, based on the response patterns, the analytics system 400 may be configured to predict how a user would handle a given fault code. That is, a given response pattern may be indicative of an expected behavior for a particular fault code. In some cases, predicting how a user would handle a given fault code may involve the analytics system 400 utilizing a machine learning model, such as a Naive Bayes model or the like.

Based at least on the response patterns, the analytics system 400 may be configured to perform a number of operations. For example, one such operation may involve handling operating data indicating a particular fault code in accordance with a predicted behavior for that particular fault code. Specifically, if the response pattern indicates that users typically disregard or ignore a particular type of fault code, the analytics system 400 may carry out an operation in accordance with this response pattern when operating data indicates a triggering of the fault code. Numerous operations may be performed in accordance with response patterns, such as causing an output system 108 to modify how a fault code is displayed to a user or suppressing a fault code altogether.

For example, the analytics system 400 may be configured to modify a fault code presentation based on response patterns and current operating data. In particular, the analytics system 400 may determine a recommended response for a given fault code based on the response patterns and current operating data. Thereafter, the analytics system 400 may transmit to the output system 108 fault-code presentation data reflecting a recommended action for a user to take with respect to the given fault code.

Figure 8B:
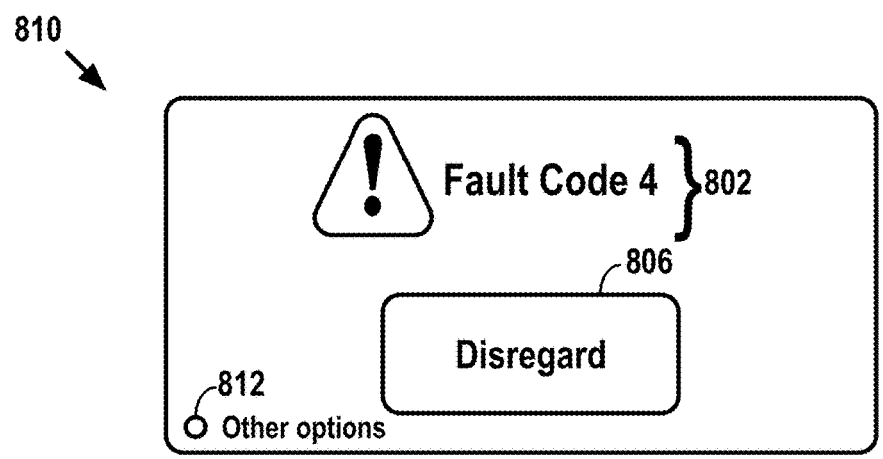
FIG. 8B depicts another example visual indication of an abnormal-condition indicator.

FIG. 8B depicts an example visual indication 810 of a fault code that may be displayed in response to receiving fault-code presentation data. As shown, the visual indication 810 is similar in some respects to the visual indication 800 from FIG. 8A. However, in the visual indication 810 the dismiss icon 806 is positioned in middle of the visual indication 810 and the action icon 804 from FIG. 8A is replaced by an other-options icon 812 that, once selected, may display the action icon 804 in a manner similar as to in FIG. 8A. In this example, the analytics system 400 may have determined that Fault Code 4 is historically dismissed or ignored and thus, determined a recommended response that the fault alert 802 be disregarded. In some cases, the visual indication 810 may disappear after a certain amount of time, thereby providing a user time to view and manually dismiss Fault Code 4, while also eventually removing the fault alert 802 so as to not annoy the user about a fault that is not meaningful.

Additionally or alternatively, the analytics system 400 may be configured to determine whether to suppress a fault code based on the response patterns and current operating data. That is, the analytics system 400 may be configured to suppress a fault code if the response patterns indicate that such fault codes are historically dismissed or ignored. Specifically, the analytics system 400 receive fault code data and/or sensor data indicating a given fault code and may identify a response pattern corresponding to the given fault code and determine whether or not to suppress the fault code (e.g., whether or not to provide fault code data to an output system 108) based on that response pattern.

In some cases, based on the fault and/or subsystem associated with fault, the analytics system 400 may be configured to determine whether the response pattern satisfies certain minimum criteria before suppressing a fault code. Example minimum criteria may include a number of responses, such as a minimum number of previous dismissals and/or ignores or a minimum percentage of dismissals and/or ignores. In some cases, the analytics system 400 may be configured to compare the underlying response counters of the given response pattern or a value derived therefrom to such minimum criteria and determine whether or not to suppress the fault code.

In some implementations, there may be multiple levels of minimum criteria, which may be determined based on the severity of the fault identified by a particular fault code and/or a subsystem associated with the particular fault code. Each tier of minimum criteria may correspond to a different response by the analytics system 400. For example, a first minimum percentage of dismissals may correspond to an adjustment of a display option (e.g., similar to that shown in FIG. 8B), a second, higher percentage of dismissals may correspond to another adjustment of a display option (e.g., such as removing the other-option icon 812), and a third, even higher percentage of dismissals may correspond to the analytics system 400 suppressing the fault code altogether. Other examples are also possible.

Moreover, the minimum criteria to suppress one fault code may differ from those of another fault code, which may depend on the fault and/or subsystem associated with the fault code. For instance, some fault codes (e.g., those associated with critical subsystems) may require a first number of dismissals before being suppressed, whereas other fault codes (e.g., those associated with non-critical subsystems) may be suppressed based on a second number of dismissals or ignores, which may be the same or less than the first number. Other examples are also possible.

Another operation that the analytics system 400 may perform based at least on the response patterns may involve generating new or updating existing fault-code rules. In particular, based on how users respond to a given fault code, the analytics system 400 may modify the sensor criteria for the given fault code. The analytics system 400 may be configured to transmit these new or updated rules to the asset 200 and/or other assets, perhaps from the same fleet of assets. In this way, the next instance where operating conditions satisfy the old fault-code rule would no longer trigger a fault code alert at the assets.

Further still, the analytics system 400 may be configured to adjust response patterns to account for the influence of environment-dependent data. In particular, the analytics system 400 may be configured to determine whether environmental factors, such as ambient temperatures, are contributing to fault codes being triggered that, without the environmental factors, would not be triggered. In the event external data indicates that an environmental factor is influencing the triggering of a fault code, the analytics system 400 may be configured to suppress the fault code. For example, external weather data may indicate that the ambient temperature is relatively high, which may contribute to the triggering of a temperature-based fault code. The analytics system 400 may suppress such a fault code based at least on the external weather data.

Moreover, the analytics system 400 may be configured to intelligently handle operating conditions that traditionally result in generating a fault code based in part on the location of the asset 200. In particular, the analytics system 400 may correlate particular user responses for certain fault codes to a given geospatial location. The analytics system 400 may then cause the asset 200 to suppress certain fault codes when the asset 200 is within a particular threshold proximity to the given geospatial location. Other examples are possible as well.

In some example implementations, a given user that reviews fault codes for a particular asset, such as an operator of a locomotive or a technician of an MRI machine, may individualize how fault codes corresponding to the particular asset are displayed to the given user. That is, the given user may override how the analytics system 400 has determined to handle certain fault codes. In the event the given user decides to do so, the analytics system 400 may receive an indication of the override and perhaps update how the analytics system 400 has determined to handle the certain fault codes, which may in turn modify how the certain fault codes are presented to other users in the future.

Specifically, the output system 108 may display to a user of a given asset an option to modify how some or all fault codes are handled for the given asset, which may involve modifying minimum criteria corresponding to the suppression of certain fault codes and/or modifying the predicted behavior for some fault codes.

For example, the output system 108 may display a selectable "preferences" element or the like that, once selected, allows the user to override the analytics system 400's recommended handling of some or all fault codes for the given asset. For instance, the user may select that Fault Code 4 be displayed as in the visual indication 800 of FIG. 8A instead of as in the visual indication 810 of FIG. 8B or the user may select that Fault Code 4 should not be suppressed, among other examples.

In another example, the output system 108 may display a selectable override element or the like the first time a fault code is being suppressed. For instance, the first time a fault code is being suppressed, the user may receive a warning indicating that the particular fault code is being suppressed along with an override icon operable to override the suppression. The user may select the override icon to override the analytics system 400's recommended suppression of the fault code.

In any event, the output system 108 may be configured to provide to the analytics system 400 override data indicating a user overriding how the analytics system 400 handles a given fault code. Based on the override data, the analytics system 400 may modify its predicted behavior for the given fault code. For example, the analytics system 400 may modify (e.g., increase or decrease) minimum criteria to suppress the given fault code and/or may modify how the given fault code is presented to or suppressed from a user.

In some implementations, the analytics system 400 may modify its predicted behavior for a given fault code based on a threshold number of overrides for the given fault code. That is, the analytics system 400 may only modify its predicted behavior for the given fault code if a threshold number of users decided to override the analytics system 400's handling of the given fault code or a threshold total number of overrides indicating the same. Other examples are also possible.

While the above discussion was in the context of the analytics system 400 receiving feedback data from a user operating an output system 108, the above discussion may apply to feedback data from an operator on an asset interacting with output fault codes. As such, in some implementations, the analytics system 400 may be configured to determine and/or update response patterns based on feedback data from assets. In particular, an operator of an asset, such as the asset 200, may receive an indication of a fault code at a user display or the like on the asset. Based on how the operator handles the indication of the fault code, the asset may provide feedback data to the analytics system 400, which may then carry out operations in line with the above discussion.

In another example of feedback data, the analytics system 400 may generate a work order in anticipation of a particular fault code occurring in the future. After receiving the work order, a mechanic may determine that no repair is necessary. If this sequence of events occurs multiple times, the analytics system 400 may facilitate modifying (e.g., decreasing) the frequency at which an asset outputs an indication of the fault code. Conversely, if there are multiple occurrences of a mechanic finding a degree of asset damage, the analytics system 400 may facilitate modifying (e.g., increasing) the frequency at which an asset outputs an indication of the fault code.

H. Historical Health Metrics

The analytics system 400 may be configured to store health metric data corresponding to the assets 102 in the databases 406. The analytics system 400 may do so for a plurality of assets over time. From such historical health metric data, the analytics system 400 may be configured to perform a number of operations.

Figure 9:
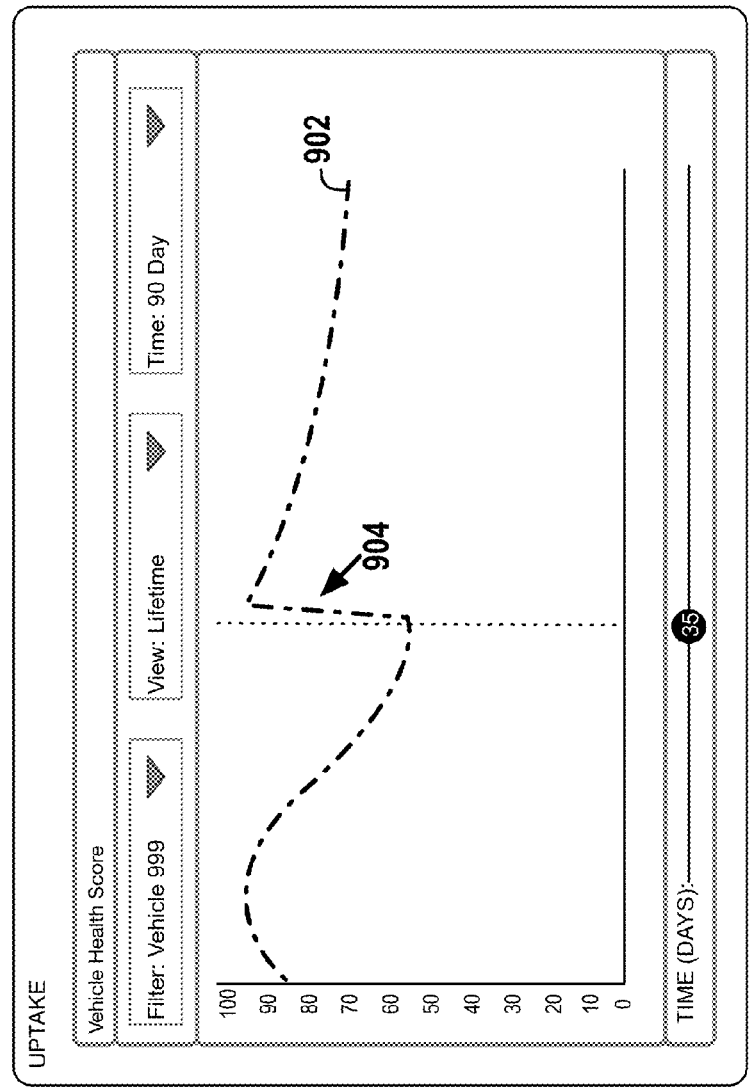
FIG. 9 depicts an example graphical user interface showing a representation of a historical health score.

In one example, the analytics system 400 may be configured to provide historical health metric data to one or more of the output systems 108, which may then display a graphical representation of the health metric. FIG. 9 depicts an example graphical user interface 900 showing a representation of a health metric over time that may be displayed by an output system 108. As shown, the graphical user interface 900 includes a health-metric curve 902 that is shown for an example period of time (e.g., 90-day period of time). In this example, a sharp change 904 in the health metric occurred around thirty-five days into the example period of time, which may indicate that a repair occurred to the asset 200 at that time. Other example representations of health metrics over time are also possible.

In another example, based at least on historical health metric data, the analytics system 400 may be configured to identify variables that influence health metrics. For instance, the analytics system 400 may be configured to analyze historical health metric data to identify variables associated with assets whose health metrics are relatively high (or relatively low). Examples of variables that may influence health metrics may include asset variables that indicate characteristics of a given asset and the operation thereof, operator variables that indicate characteristics of the human operators that operate a given asset, and maintenance variables that indicate characteristics of mechanics and the like that perform routine maintenance or repairs to a given asset, among other examples.

Examples of asset variables may include asset brand, asset model, asset travel schedules, asset payloads, and asset environment, among others. Asset brand may indicate the manufacturer of a given asset, while asset model may indicate the particular model of asset from the given manufacturer (e.g., a model identifier or the like). Asset travel schedules may indicate routes that a given asset traverses, which may include an indication of elevations, terrain, and/or travel durations. Asset payloads may indicate type and/or amount (e.g., weight) of cargo or the like that an asset hauls. Asset environment may indicate various characteristics about the environment in which a given asset is operated, such as geospatial location, climate, average ambient temperature or humidity, and/or proximity of sources of electrical interference, among other examples.

Examples of operator variables may include any variable associated with the person or persons that operate an asset, such as an operator identifier, operator schedule, and operator habits, among others. An operator identifier may identify the individual operator that operated a given asset. An operator schedule may indicate the type of shift (e.g., morning, day, night, etc.) or duration of shift (e.g., number of hours) during which a given asset is operated. Operator habits may indicate various trends in an operator's handling of a given asset, such as average braking distance, average acceleration time, average deceleration time, average RPMs, and the like.

Examples of maintenance variables may include any variable associated with the maintenance (e.g., general upkeep and/or review of operating conditions of an asset) and/or repair of an asset, such as date of maintenance or repair, time between asset checkups, location of repair, repair-shop identifier, mechanic identifier, and duration of repair time, among others. Date of maintenance or repair may indicate the date as well as time that maintenance or a repair was performed on a given asset. Time between checkups may indicate an amount of time between instances when maintenance personnel evaluated the asset for any operating problems. Location of repair may indicate where a repair was performed (e.g., at a repair shop or out in the field). Repair-shop identifier may identify the particular repair-shop or the like that repaired a given asset, while mechanic identifier may identify the particular mechanic or the like that worked on the given asset. Duration of repair time may indicate the amount of time that was spent repairing a given asset.

One of ordinary skill in the art will appreciate that the aforementioned asset-related variables are provided for purposes of example and explanation only and are not meant to be limiting. Numerous other variables are possible and contemplated herein.

In practice, the analytics system 400 may be configured to determine variables based in part on asset-related historical data stored in the databases 406 or provided by the data sources 110. Examples of such data may include manufacturer or asset technical specifications, asset travel logs, asset payload logs, weather records, maps, building electricity bills, operator time cards or the like, operator work schedules, asset operating data, maintenance or repair logs, mechanic time cards, or any other data discussed herein, among other examples.

Figure 10:
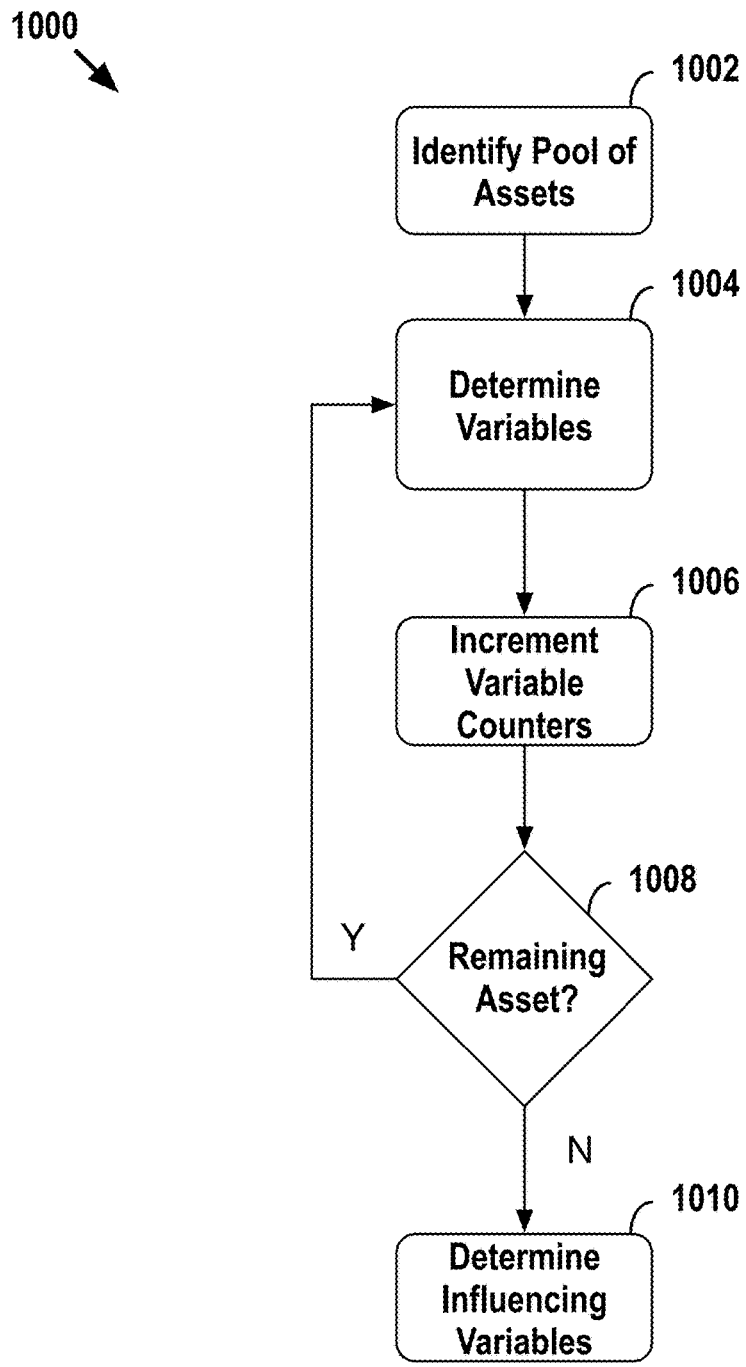
FIG. 10 depicts an example flow diagram for determining variables.

The analytics system 400 may be configured to determine variables based on historical health-metric data, and perhaps other historical asset-related data, in a number of manners. FIG. 10 depicts an example flow diagram 1000 for determining variables.

As shown, at block 1002, the analytics system 400 may be configured to identify one or more assets (collectively referred to herein as a "pool of assets") whose health metrics over time will be analyzed. In some examples, the pool of assets may include assets with relatively high health metrics. For instance, the asset pool may include each asset whose historical health metric has been above a threshold value for a particular amount of time, whose historical health metric has never dropped below a threshold value, or whose average historical health metric determined over a particular amount of time is above a threshold value, among other possibilities. In other instances, the asset pool may include a particular number of assets whose health metrics meet any of the aforementioned threshold requirements. On the other hand, in other examples, the pool of assets may include assets with relatively low health metrics.

At block 1004, for each asset in the pool of assets, the analytics system 400 may be configured to analyze the given asset's historical health-metric data and/or asset-related data to determine variables of the given asset. The analytics system 400 may do so for a given amount of time or over the whole operating life of each asset.

In practice, the analytics system 400 may be configured to determine any or all of the variables discussed above for the given asset, or the analytics system 400 may be configured to make this determination for a select subset of the variables, such as only asset attributes or only maintenance attributes, among other examples. The subset of the variables may be predefined and stored in a database 406 or dynamically determined, among other examples.

In some implementations, the analytics system 400 may be configured to determine the subset of variables based at least on the given asset's historical health-metric data. In particular, the analytics system 400 may be configured to identify trends in the given asset's historical health-metric data and determine a potential cause or causes of such a trend, perhaps from the historical asset-related data. In some cases, a trend may be a threshold amount of change (e.g., an increase or decrease) in a health metric over a certain period of time, a constant health metric for a certain amount of time, or a certain amount of increase followed by a certain amount of time prior to a threshold amount of decrease, among other examples.

In a specific example, the analytics system 400 may be configured to identify a threshold amount of increase in a historical health metric, such as an at least 10% increase, over a given period of time, such as a week. The analytics system 400 may then identify a time at which the trend began (or ended or a time in between) and analyze the asset-related data from around (e.g., a certain amount of time's worth of data before or after) the identified time to determine one or more potential causes of the change.

For instance, returning to FIG. 9, the analytics system 400 may evaluate the historical health-metric data represented by the health-metric curve 902 and determine that the sharp change 904 is greater than a 10% increase in the health metric. The analytics system 400 may then identify the date corresponding to day 35 (e.g., May 1, 2015) shown on the graphical user interface 900 and based on various asset-related data, determine any events that took place around that May $1^{st}$ date, which may indicate one or more potential causes of the sharp change 904. In one example, the analytics system 400 may determine from repair logs that, on May 5, 2015, Mechanic A at Repair Shop 1 repaired the given asset's engine. Identifiers for Repair Shop 1 and Mechanic A may then become variables.

At block 1006, the analytics system 400 may generate a record of the determined variables. In examples, the analytics system 400 may store in one of the databases 406 variable counters for each of the variables. The analytics system 400 may be configured to increment the appropriate counters corresponding to each of the determined variables. The variable counters may provide an indication of the variables that are commonly found amongst assets with relatively high health metrics.

At block 1008, the analytics system 400 may then determine whether there are any remaining assets from the pool of assets for which variables should be determined and incremented. In the event that an asset remains, the analytics system 400 may repeat the loop of blocks 1004-1008. After the analytics system 400 has determined and incremented the variables for each of assets from the asset pool, the resulting data may then provide, to some degree, an indication of variables that lead to high health metrics.

FIG. 11 depicts conceptual illustrations of data that results from incrementing variable counters. In particular, histogram 1100 depicts counters for a maintenance variable for the pool of assets. More specifically, the histogram 1100 shows that more assets repaired by Mechanic A had high health metrics than assets repaired by Mechanics B and C. Histogram 1102 depicts counters for an asset environment variable, and in particular, that fewer assets had high health metrics that operated in an environment with ambient temperatures over 45° C. than any other temperature range. Histogram 1104 depicts counters for an operator habit variable and in particular, that more assets whose operator's average acceleration time was between ten and fifteen minutes had high health metrics than other acceleration times. Histogram 1106 depicts a counter for an asset variable that indicates that more assets of the type Brand A Model 7 had high health metrics than the other two model types. One of ordinary skill in the art will appreciate that these are but a few example variables and that numerous other variables are possible.

Returning to FIG. 10, at block 1010, the analytics system 400 may be configured to determine influencing variables based in part on the variable counters. In some examples, the influencing variables are variables whose variable counters exceed a predetermined threshold value. In other examples, the influencing variables are variables whose variable counters have a maximized value. For instance, referring to the histogram 1100, Mechanic A may be determined to be an influencing variable because the variable counter for Mechanic A has the highest value of the other counters. Other examples are also possible.

The analytics system 400 may determine influencing variables in a variety of other manners. For example, in other implementations, the analytics system 400 may determine influencing variables by first determining a pool of assets in line with block 1002 of FIG. 10 and then analyzing asset-related data for each of the assets from the pool of assets. The analytics system 400 may identify variables that the assets from the pools of assets have in common. These identified variables may then be defined as the influencing variables or a subset of the identified variables may be defined as the influencing variables (e.g., those variables that a threshold number of assets from the pool of assets have in common). Other manners for determining influencing variables are also possible.

After determining the influencing variables, the analytics system 400 may be configured to perform a number of operations. For example, the analytics system 400 may be configured to determine various recommendations with respect to assets, perhaps determining a ranked list of recommendations, and then cause a graphical display to output an indication of such recommendations to a user. In general, a given recommendation may be a general recommendation (e.g., a fleet-wide recommendation), such as that all assets should be operated at less than 75% capacity, or an asset- or asset-group-specific recommendation, such as that particular assets should be sent to a certain repair shop to get a specific repair performed.

Moreover, a given recommendation may be based on determining that a particular asset has a relatively low health metric and then evaluating variables of the particular asset. The given recommendation may then facilitate modifying the variables of the particular asset to more closely align with the influencing variables determined at block 1010.

Example recommendations may include recommended brands or models of assets to purchase, recommended repair shops or individual mechanics for future repairs, recommended repair schedules for one or more assets, recommended operators for future work shifts, recommended instructions for teaching operators to efficiently operate assets, and recommended location or environment to operate an asset, among other examples.

In other examples, the analytics system 400 may be configured to transmit an operating command to an asset that facilitates causing the asset to be operated in accordance with an influencing variable. For example, from the variable data represented graphically by the histogram 1104, the analytics system 400 may transmit instructions to assets where the instructions restrict how quickly the assets may be accelerated thereby bringing the operation of the assets closer to the average 10-15 minute acceleration time. Other examples are also possible.

Additionally or alternatively, the analytics system 400 may be configured to perform other operations based on historical health-metric data. In one example, the analytics system 400 may be configured to modify a health-metric module. Specifically, the analytics system 400 may trigger the generation of a work order based on a health metric reaching a particular threshold value. Thereafter, the analytics system 400 may then monitor the health metric data for a threshold amount of time. In the event that the health metric increases a certain amount within a predetermined amount of time after generating the work order, the analytics system 400 may be configured to infer that the work order to repair the particular component was performed and fixed the cause of the declining health metric. Based on this inference, the analytics system 400 may be configured to modify a health-metric model and/or actions triggered based off the health-metric model. Other examples are also possible.

V. Example Methods

Figure 12:
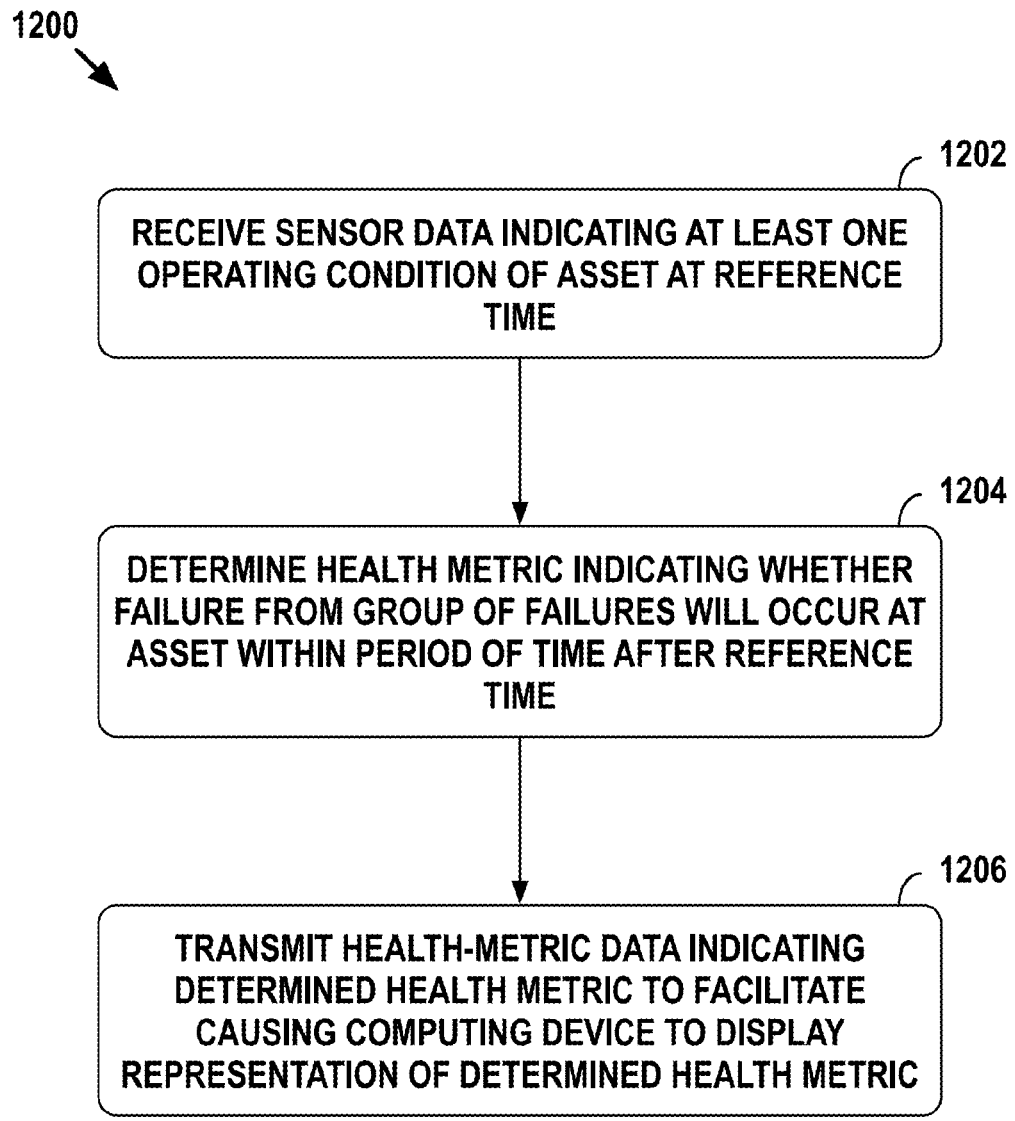
FIG. 12 depicts a flow diagram of an example method for determining a health score.

Turning now to FIG. 12, a flow diagram is depicted illustrating an example method 1200 for determining a health metric that may be performed by the analytics system 400. For the method 1200 and the other methods discussed below, the operations illustrated by the blocks in the flow diagrams may be performed in line with the above discussion. Moreover, one or more operations discussed above may be added to a given flow diagram.

At block 1202, the method 1200 may involve the analytics system 400 receiving sensor data indicating at least one operating condition of an asset (e.g., the asset 200) at a reference time, such as a present point in time. At block 1204, the method 1200 may involve the analytics system 400, based on the received sensor data and historical operating data (e.g., stored in the databases 406), determining a health metric indicating whether a failure from a group of failures will occur at the asset within a period of time after the reference time, such as two-weeks after the present time. The historical operating data includes at least (i) historical abnormal-condition data associated with a failure that occurred at the asset at a past time (e.g., a time during a two-week period of time before the present point in time) and (ii) historical sensor data indicating at least one operating condition of the asset at the past time. At block 1206, the method 1200 may involve the analytics system 400 transmitting to a computing device (e.g., of an output system 108) health-metric data indicating the determined health metric to facilitate causing the computing device to display a representation of the determined health metric, such as a visual and/or audible representation.

Figure 13:
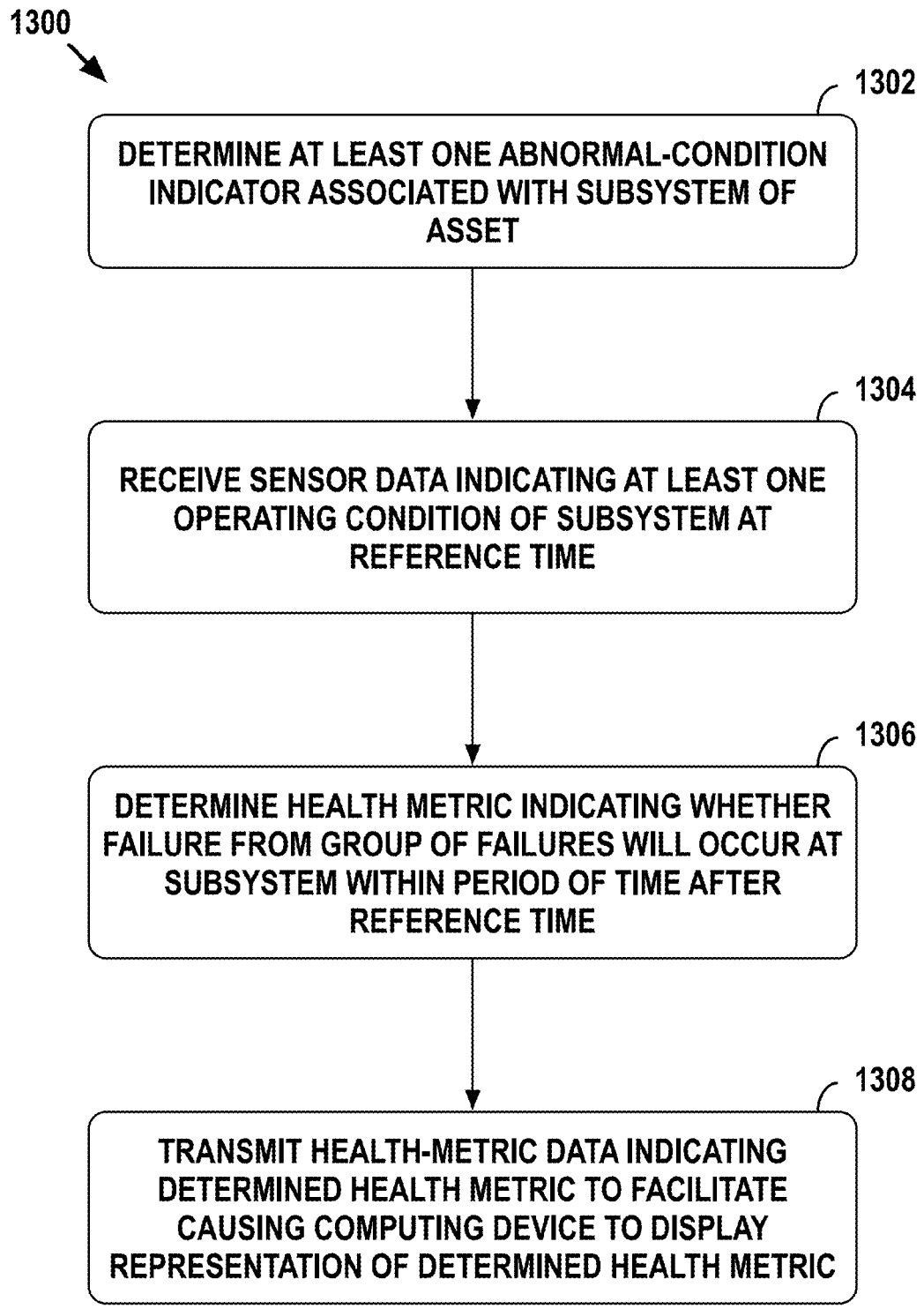
FIG. 13 depicts a flow diagram of an example method for determining a health score for a subsystem of an asset.

FIG. 13 depicts a flow diagram of an example method 1300 for determining a health metric for a subsystem of an asset that may be performed by the analytics system 400. At block 1302, the method 1300 may involve the analytics system 400, based at least on historical operating data, determining at least one abnormal-condition indicator (e.g., a fault code) associated with a subsystem of an asset, such as a subsystem 202 of the asset 200. The historical operating data includes at least (i) historical abnormal-condition data associated with a failure that occurred at the subsystem at a past time, such as a time during the two weeks prior to a present point in time, and (ii) historical sensor data indicating at least one operating condition of the subsystem at the past time. At block 1304, the method 1300 may involve the analytics system 400 receiving sensor data indicating at least one operating condition of the subsystem at a reference time, such as the present point in time. At block 1306, the method 1300 may involve the analytics system 400, based on (i) the received sensor data, (ii) the determined at least one abnormal-condition indicator, and (iii) the historical operating data, determining a health metric indicating whether a failure from a group of failures will occur at the subsystem within a period of time after the reference time, such as a week after the present time. At bock 1308, the method 1300 may involve the analytics system 400 transmitting to a computing device (e.g., of an output system 108) health-metric data indicating the determined health metric to facilitate causing the computing device to display a representation of the determined health metric.

Figure 14:
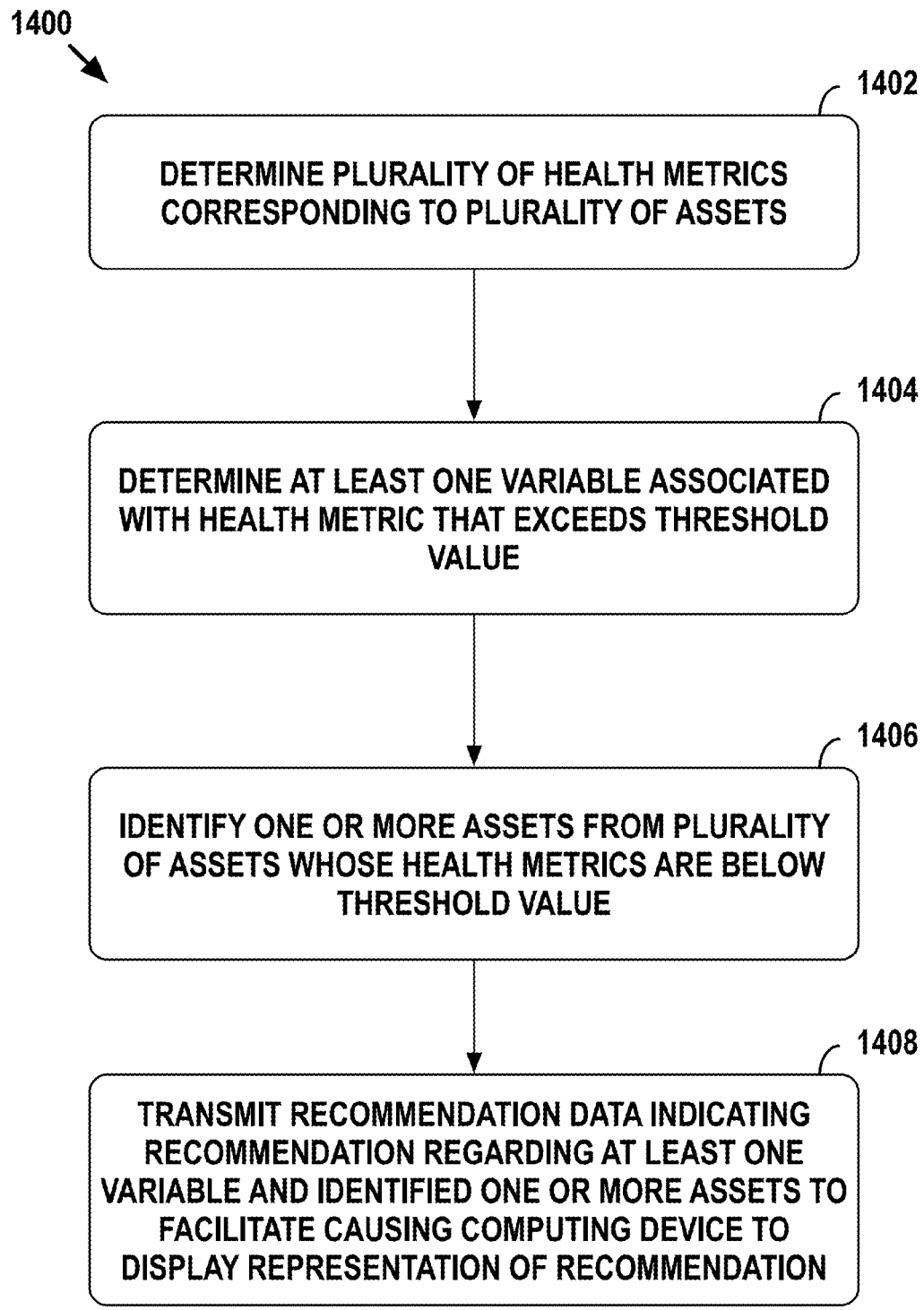
FIG. 14 depicts a flow diagram of an example method for making recommendations based on variables associated with high health scores.

FIG. 14 depicts a flow diagram of an example method 1400 for making recommendations based on asset-related variables associated with high health metrics that may be performed by the analytics system 400. At block 1402, the method 1400 may involve the analytics system 400, based on a plurality of operating data, determining a plurality of health metrics corresponding to a plurality of assets (e.g., the assets 102). A given health metric indicates whether a failure from a group of failures will occur at a given asset within a period of time. At block 1404, the method 1400 may involve the analytics system 400, based at least on the plurality of health metrics, determining at least one variable associated with a health metric that exceeds a threshold value. At block 1406, the method 1400 may involve the analytics system 400, based on the determined at least one variable, identifying one or more assets from the plurality of assets whose health metrics are below the threshold value. At block 1408, the method 1400 may involve the analytics system 400 transmitting to a computing device (e.g., of an output system 108) recommendation data indicating a recommendation regarding the at least one asset-related variable and the identified one or more assets to facilitate causing the computing device to display a representation of the recommendation.

Figure 15:
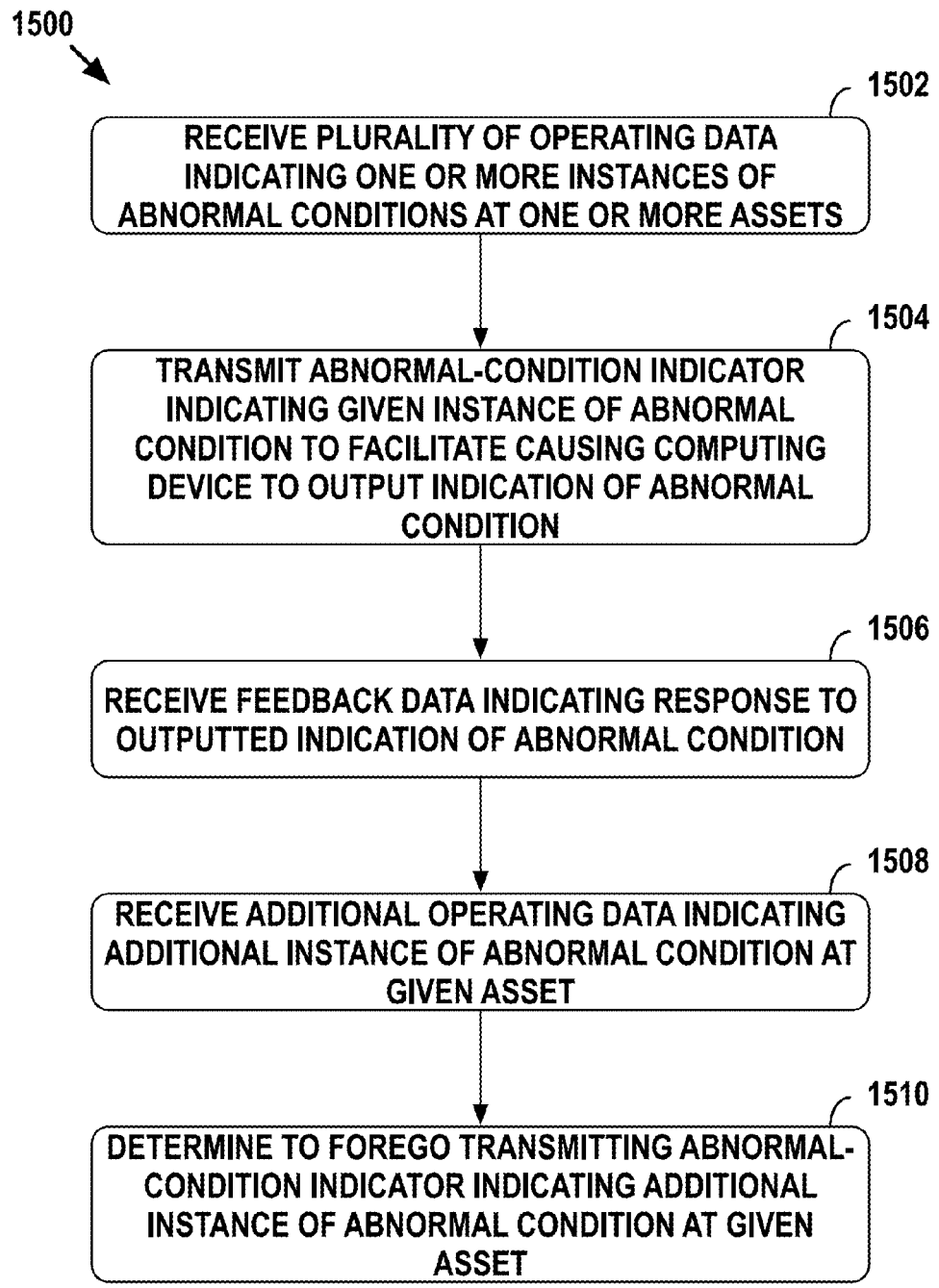
FIG. 15 depicts a flow diagram of an example method for modifying the handling of operating data that normally result in an abnormal-condition indicator.

FIG. 15 depicts a flow diagram of an example method 1500 for modifying the handling of operating data that normally result in an abnormal-condition indicator that may be performed by the analytics system 400. At block 1502, the method 1500 may involve the analytics system 400 receiving a plurality of operating data indicating one or more instances of an abnormal condition at one or more assets (e.g., the assets 102). At block 1504, for each of the one or more instances of the abnormal condition, the method 1500 may involve the analytics system 400 transmitting to a computing device (e.g., of an output system 108) an abnormal-condition indicator (e.g., fault code data) indicating a given instance of the abnormal condition to facilitate causing the computing device to output an indication of the abnormal condition. At block 1506, for each of the one or more instances of the abnormal condition, the method 1500 may involve the analytics system 400 receiving feedback data indicating a response to the outputted indication of the abnormal condition. At block 1508, the method 1500 may involve the analytics system 400 receiving additional operating data indicating an additional instance of the abnormal condition at a given asset. At block 1510, the method 1500 may involve the analytics system 400, based on the received feedback data and the received additional operating data, determining to forego transmitting to the computing device an abnormal-condition indicator indicating the additional instance of the abnormal condition at the given asset.

To the extent that examples described herein involve operations performed or initiated by actors, such as "humans", "operators", "users" or other entities, this is for purposes of example and explanation only. The claims should not be construed as requiring action by such actors unless explicitly recited in the claim language.

What is claimed is:

1. A computing system comprising:
   a network interface configured to facilitate communication with a plurality of assets equipped with sensors and a plurality of computing devices;
   at least one processor;
   a non-transitory computer-readable medium; and
   program instructions stored on the non-transitory computer-readable medium that are executable by the at least one processor to cause the computing system to:
   for each respective failure type of a group of failure types:
   (i) identify one or more types of abnormal-condition indicators associated with a respective failure type,
   (ii) identify past instances of the identified one or more types of abnormal-condition indicators at the plurality of assets equipped with sensors, wherein each past instance of a respective type of abnormal-condition indicator is indicative of a past occurrence of a respective type of abnormal condition at one asset of the plurality of assets,
   (iii) identify historical sensor data corresponding to the identified past instances of the identified one or more types of abnormal-condition indicators, wherein the historical sensor data for each past instance of a respective type of abnormal-condition indicator indicates operating conditions of the one asset associated with a past occurrence of a respective type of abnormal condition at the one asset, and
   (iv) apply a supervised machine learning technique to the identified historical sensor data to define a respective predictive model for the respective failure type that is configured to receive sensor data for the one asset as input and
   output a value indicating whether the respective failure type is likely to occur at the one asset within a given period of time in the future;
   combine the respective predictive models for the group of failure types into an aggregated predictive model that is configured to receive sensor data for the one asset as input and output a health metric indicating whether at least one failure type from the group of failure types is likely to occur at the one asset within a given period of time in the future;
   receive sensor data indicating operating conditions of a given asset;
   apply the aggregated predictive model to the received sensor data to determine, for the given asset, a health metric indicating whether at least one failure type from the group of failure types is likely to occur at the given asset within the given period of time in the future;
   detect that the health metric for the given asset satisfies threshold criteria; and
   in response to the detection, cause a computing device to display a visual indicator that at least one failure type from the group of failure types is likely to occur at the given asset.

2. The computing system of claim 1, wherein the group of failure types comprises one or more failure types that could render the given asset inoperable when the one or more failure types occur.

3. The computing system of claim 1, wherein the health metric for the given asset comprises one of (i) a probability that no failure type from the group of failure types will occur at the given asset within the given period of time in the future or (ii) a probability that at least one failure type from the group of failure types will occur at the given asset within the given period of time in the future.

4. The computing system of claim 1, wherein the program instructions are further executable by the at least one processor to cause the computing system to:
   in response to the detection that the health metric for the given asset satisfies the threshold criteria, carry out a remedial action to facilitate increasing the operating health of the given asset.

5. The computing system of claim 4, wherein carrying out the remedial action comprises one or more of (a) automatically generating and sending, to a computing device associated with an individual responsible for overseeing the given asset, an alert indicating that the given asset is considered to be in a state of impending failure, (b) automatically generating and sending, to the given asset, an instruction for the given asset to modify its operation to account for the detection that the given asset is considered to be in a state of impending failure, (c) automatically generating and sending, to a repair facility, an instruction to repair the given asset, and (d) automatically generating and sending, to a parts-ordering system, an instruction for the parts ordering system to order a given component of the given asset.

6. The computing system of claim 5, wherein the alert indicating that the given asset is considered to be in a state of impending failure includes an indication of one or more recommended repairs to the given asset.

7. The computing system of claim 4, wherein the remedial action is one given remedial action from a plurality of remedial actions, and wherein the program instructions are further executable by the at least one processor to cause the computing system to:
   after carrying out the given remedial action, determine feedback data associated with carrying out the given remedial action; and
   based on the feedback data, prioritize the given remedial action over other remedial actions from the plurality of remedial actions.

8. The computing system of claim 1, wherein the group of failure types is defined based on user input.

9. A non-transitory computer-readable medium having instructions stored thereon that are executable to cause a computing system to:
   for each respective failure type of a group of failure types:
   (i) identify one or more types of abnormal-condition indicators associated with a respective failure type,
   (ii) identify past instances of the identified one or more types of abnormal-condition indicators at a plurality of assets equipped with sensors, wherein each past instance of a respective type of abnormal-condition indicator is indicative of a past occurrence of a respective type of abnormal condition at one asset of the plurality of assets,
   (iii) identify historical sensor data corresponding to the identified past instances of the identified one or more types of abnormal-condition indicators, wherein the historical sensor data for each past instance of a respective type of abnormal-condition indicator indicates operating conditions of the one asset associated with a past occurrence of a respective type of abnormal condition at the one asset, and (iv) apply a supervised machine learning technique to the identified historical sensor data to define a respective predictive model for the respective failure type that is configured to receive sensor data for the one asset as input and output a value indicating whether the respective failure type is likely to occur at the one asset within a given period of time in the future;

combine the respective predictive models for the group of failure types into an aggregated predictive model that is configured to receive sensor data for the one asset as input and output a health metric indicating whether at least one failure type from the group of failure types is likely to occur at the one asset within a given period of time in the future;

receive sensor data indicating operating conditions of a given asset;

apply the aggregated predictive model to the received sensor data to determine, for the given asset, a health metric indicating whether at least one failure type from the group of failure types is likely to occur at the given asset within the given period of time in the future; and detect that the health metric for the given asset satisfies threshold criteria; and in response to the detection, cause a computing device to display a visual indicator that at least one failure type from the group of failure types is likely to occur at the given asset.

10. The non-transitory computer-readable medium of claim 9, wherein the instructions are further executable to cause the computing system to:

in response to the detection that the health metric for the given asset satisfies the threshold criteria, carry out a remedial action to facilitate increasing the operating health of the given asset.

11. The non-transitory computer-readable medium of claim 10, wherein carrying out the remedial action comprises one or more of (a) automatically generating and sending, to a computing device associated with an individual responsible for overseeing the given asset, an alert indicating that the given asset is considered to be in a state of impending failure, (b) automatically generating and sending, to the given asset, an instruction for the given asset to modify its operation to account for the detection that the given asset is considered to be in a state of impending failure, (c) automatically generating and sending, to a repair facility, an instruction to repair the given asset, and (d) automatically generating and sending, to a parts-ordering system, an instruction for the parts ordering system to order a given component of the given asset.

12. The non-transitory computer-readable medium of claim 11, wherein the alert indicating that the given asset is considered to be in a state of impending failure includes an indication of one or more recommended repairs to the given asset.

13. The non-transitory computer-readable medium of claim 9, wherein the health metric for the given asset comprises one of (i) a probability that no failure type from the group of failure types will occur at the given asset within the given period of time in the future or (ii) a probability that at least one failure type from the group of failure types will occur at the given asset within the given period of time in the future.

14. The non-transitory computer-readable medium of claim 9, wherein the group of failure types is defined based on user input.

15. A computer-implemented method, the method comprising:

for each respective failure type of a group of failure types:
(i) identifying one or more types of abnormal-condition indicators associated with a respective failure type,
(ii) identifying past instances of the identified one or more types of abnormal-condition indicators at a given set of assets equipped with sensors, wherein each past instance of a respective type of abnormal-condition indicator is indicative of a past occurrence of a respective type of abnormal condition at one asset of the plurality of assets,
(iii) identifying historical sensor data corresponding to the identified past instances of the identified one or more types of abnormal-condition indicators at the plurality of assets, wherein the historical sensor data for each past instance of a respective type of abnormal-condition indicator indicates operating conditions of the one asset associated with a past occurrence of a respective type of abnormal condition at the one asset, and
(iv) applying a supervised machine learning technique to the identified historical sensor data to define a respective predictive model for the respective failure type that is configured to receive sensor data for the one asset as input and output a value indicating whether the respective failure type is likely to occur at the one asset within a given period of time in the future;

combining the respective predictive models for the group of failure types into an aggregated predictive model that is configured to receive sensor data for the one asset as input and output a health metric indicating whether at least one failure type from the group of failure types is likely to occur at the one asset within a given period of time in the future;

receiving sensor data indicating operating conditions of a given asset;

applying the aggregated predictive model to the received sensor data to determine, for the given asset, a health metric indicating whether at least one failure type from the group of failure types is likely to occur at the given asset within the given period of time in the future;

detecting that the health metric for the given asset satisfies threshold criteria; and in response to the detecting, causing a computing device to display a visual indicator that at least one failure type from the group of failure types is likely to occur at the given asset.

16. The computer-implemented method of claim 15, wherein the health metric for the given asset comprises one of (i) a probability that no failure type from the group of failure types will occur at the given asset within the given period of time in the future or (ii) a probability that at least one failure type from the group of failure types will occur at the given asset within the given period of time in the future.

17. The computer-implemented method of claim 15, further comprising:

in response to detecting that the health metric for the given asset satisfies the threshold criteria, carry out a remedial action to facilitate increasing the operating health of the given asset.

18. The computer-implemented method of claim 17, wherein carrying out the remedial action comprises one or more of (a) automatically generating and sending, to a computing device associated with an individual responsible for overseeing the given asset, an alert indicating that the given asset is considered to be in a state of impending failure, (b) automatically generating and sending, to the given asset, an instruction for the given asset to modify its operation to account for the detection that the given asset is considered to be in a state of impending failure, (c) automatically generating and sending, to a repair facility, an instruction to repair the given asset, and (d) automatically generating and sending, to a parts-ordering system, an instruction for the parts ordering system to order a given component of the given asset.

19. The computer-implemented method of claim 18, the alert indicating that the given asset is considered to be in a state of impending failure includes an indication of one or more recommended repairs to the given asset.

20. The computer-implemented method of claim 15, wherein the group of failure types is defined based on user input.

* * * * *